United States Patent
Venkatraman et al.

(10) Patent No.: US 11,357,651 B2
(45) Date of Patent: Jun. 14, 2022

(54) STENT ASSEMBLY AND METHOD OF PREPARING THE STENT ASSEMBLY

(71) Applicants: Nanyang Technological University, Singapore (SG); Singapore Health Services Pte. Ltd., Singapore (SG)

(72) Inventors: Subramaniam Venkatraman, Singapore (SG); Yingying Huang, Singapore (SG); Wei Shan Lim, Singapore (SG); Tsung Wen Chong, Singapore (SG)

(73) Assignees: Nanyang Technological University, Singapore (SG); Singapore Health Services Pte. Ltd., Singapore (SG)

( * ) Notice: Subject to any disclaimer, the term of this patent is extended or adjusted under 35 U.S.C. 154(b) by 714 days.

(21) Appl. No.: 15/559,755

(22) PCT Filed: Mar. 15, 2016

(86) PCT No.: PCT/SG2016/050119
§ 371 (c)(1),
(2) Date: Sep. 19, 2017

(87) PCT Pub. No.: WO2016/148648
PCT Pub. Date: Sep. 22, 2016

(65) Prior Publication Data
US 2018/0042742 A1    Feb. 15, 2018

(30) Foreign Application Priority Data

Mar. 19, 2015  (SG) ........................... 10201502162X

(51) Int. Cl.
*A61F 2/94*    (2013.01)
*A61F 2/04*    (2013.01)
(Continued)

(52) U.S. Cl.
CPC ................. *A61F 2/94* (2013.01); *A61F 2/04* (2013.01); *A61K 31/337* (2013.01);
(Continued)

(58) Field of Classification Search
CPC ........ A61L 31/10; A61L 31/16; A61L 31/145; A61L 27/507; A61L 2300/40;
(Continued)

(56) References Cited

U.S. PATENT DOCUMENTS 4,733,665 A * 3/1988 Palmaz ................... A61F 2/915
606/108
4,800,882 A * 1/1989 Gianturco ............. B21F 45/008
606/194
(Continued)

FOREIGN PATENT DOCUMENTS

| JP | 2007-229123 A | 9/2007 |
|---|---|---|
| WO | 2010/093427 A2 | 8/2010 |
| WO | 2011/005840 A2 | 1/2011 |

OTHER PUBLICATIONS

Sands et al, "Advances in Understanding Urine-Concentrating Mechanism", (Feb. 2014), Annu. Rev. Physiol., 76:387-409. (Year: 2014).*

*Primary Examiner* — Paul B Prebilic
(74) *Attorney, Agent, or Firm* — Seed IP Law Group LLP

(57) ABSTRACT

Various embodiments relate to a stent assembly comprising a stent; a swellable coating disposed on at least a portion of an exterior surface of the stent; optionally, a carrier dispersed in the swellable coating and/or disposed on at least a portion of an exterior surface of the stent; and an active (Continued)

agent comprised in at least one of the swellable coating or the carrier, if present. Use of the stent assembly as a ureteric stent, and method of preparing a stent assembly are also provided.

14 Claims, 23 Drawing Sheets

(51) Int. Cl.

| | |
|---|---|
| *A61L 31/10* | (2006.01) |
| *A61F 2/82* | (2013.01) |
| *A61L 31/14* | (2006.01) |
| *A61L 31/16* | (2006.01) |
| *A61K 31/337* | (2006.01) |
| *A61K 31/407* | (2006.01) |
| *A61K 31/505* | (2006.01) |
| *A61M 27/00* | (2006.01) |

(52) U.S. Cl.
CPC .......... *A61K 31/407* (2013.01); *A61K 31/505* (2013.01); *A61L 31/10* (2013.01); *A61L 31/145* (2013.01); *A61L 31/148* (2013.01); *A61L 31/16* (2013.01); *A61F 2002/048* (2013.01); *A61F 2210/0004* (2013.01); *A61F 2210/0061* (2013.01); *A61F 2210/0071* (2013.01); *A61F 2240/001* (2013.01); *A61F 2250/0067* (2013.01); *A61L 2300/416* (2013.01); *A61L 2420/02* (2013.01); *A61L 2420/06* (2013.01); *A61M 27/008* (2013.01)

(58) Field of Classification Search
CPC ............. A61L 2300/41; A61L 2300/42; A61L 2300/402; A61L 2300/416; A61L 2300/412; A61L 2300/432; A61L 2300/606; A61L 2300/608; A61L 2300/61; A61L 2300/62–626; A61L 2420/04; A61L 2420/08; A61L 2430/36; A61L 31/148; A61L 2420/02; A61L 2420/06; A61F 2/82; A61F 2002/048; A61F 2210/0076; A61F 2250/0067; A61F 2250/0068; A61F 2/94; A61F 2/04; A61F 2210/0004; A61F 2210/0061; A61F 2210/0071; A61F 2240/001
See application file for complete search history.

(56) References Cited

U.S. PATENT DOCUMENTS

| | | | | |
|---|---|---|---|---|
| 4,841,962 | A * | 6/1989 | Berg | A61K 9/70 128/DIG. 8 |
| 4,886,062 | A * | 12/1989 | Wiktor | B21F 45/008 606/194 |
| 5,464,650 | A * | 11/1995 | Berg | A61L 31/10 427/2.3 |
| 5,605,696 | A * | 2/1997 | Eury | A61P 7/02 623/1.42 |
| 5,954,706 | A | 9/1999 | Sahatjian | |
| 6,120,904 | A | 9/2000 | Hostettler et al. | |
| 7,550,005 | B2 * | 6/2009 | Bates | A61L 33/022 623/1.15 |
| 8,110,242 | B2 | 2/2012 | Hawkins et al. | |
| 9,060,888 | B2 * | 6/2015 | Gellman | A61F 2/88 |
| 2001/0007083 | A1 | 7/2001 | Roorda | |
| 2002/0035168 | A1 | 3/2002 | Loomis et al. | |
| 2002/0133183 | A1 * | 9/2002 | Lentz | C08L 27/16 606/155 |
| 2003/0100830 | A1 | 5/2003 | Zhong et al. | |
| 2003/0125803 | A1 * | 7/2003 | Vallana | A61L 31/16 623/1.42 |
| 2004/0086568 | A1 | 5/2004 | Ditizio et al. | |
| 2004/0098106 | A1 | 5/2004 | Williams et al. | |
| 2004/0249443 | A1 * | 12/2004 | Shanley | A61F 2/91 623/1.15 |
| 2005/0143808 | A1 | 6/2005 | Hossainy et al. | |
| 2006/0002974 | A1 | 1/2006 | Pacetti et al. | |
| 2006/0034931 | A1 * | 2/2006 | Hansen | A61L 31/16 424/486 |
| 2006/0129225 | A1 * | 6/2006 | Kopia | A61B 17/115 623/1.13 |
| 2012/0089218 | A1 | 4/2012 | Dardi | |
| 2012/0197385 | A1 * | 8/2012 | Anzai | A61F 2/91 623/1.15 |
| 2012/0216914 | A1 * | 8/2012 | Pacetti | A61F 2/91 141/65 |
| 2013/0203697 | A1 * | 8/2013 | Hashimoto | A61Q 19/08 514/54 |
| 2013/0296806 | A1 * | 11/2013 | Li | A61L 27/54 604/264 |
| 2021/0283315 | A1 * | 9/2021 | Wang | A61L 29/16 |

* cited by examiner

FIG. 11
(A) 2.5% MMC, no PEGDA
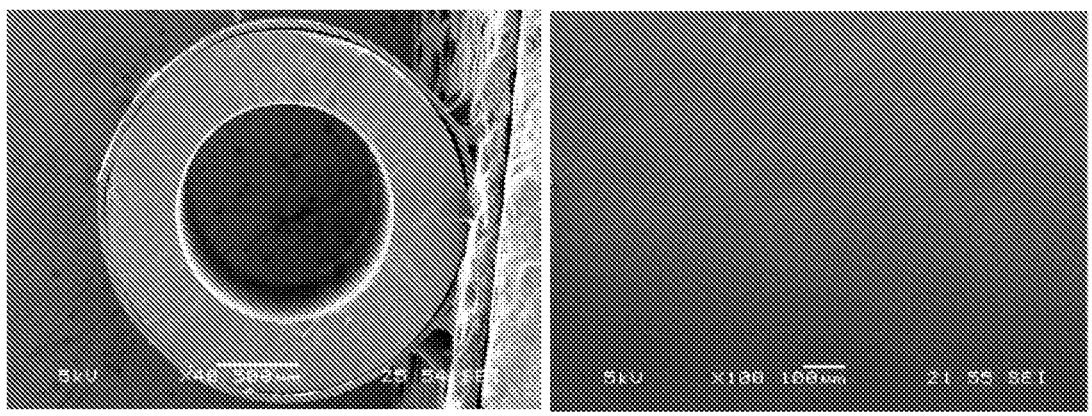
(B) 5% MMC, no PEGDA
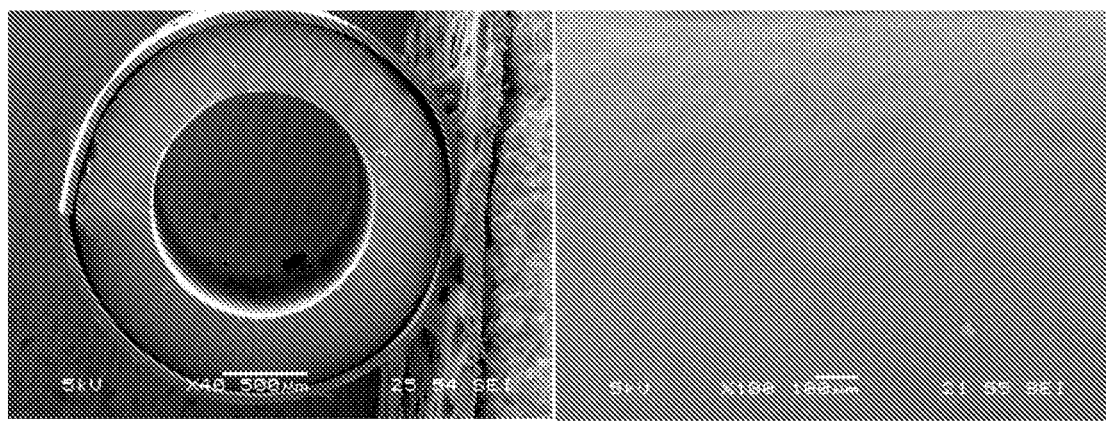

FIG. 11 (Cont.)
(C) 7.5% MMC, no PEGDA
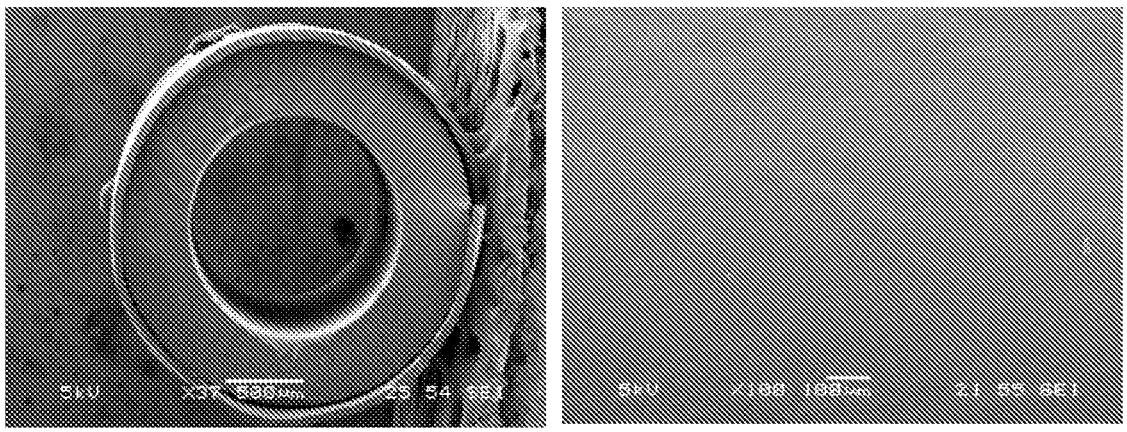
(D) 5% MMC, with PEGDA
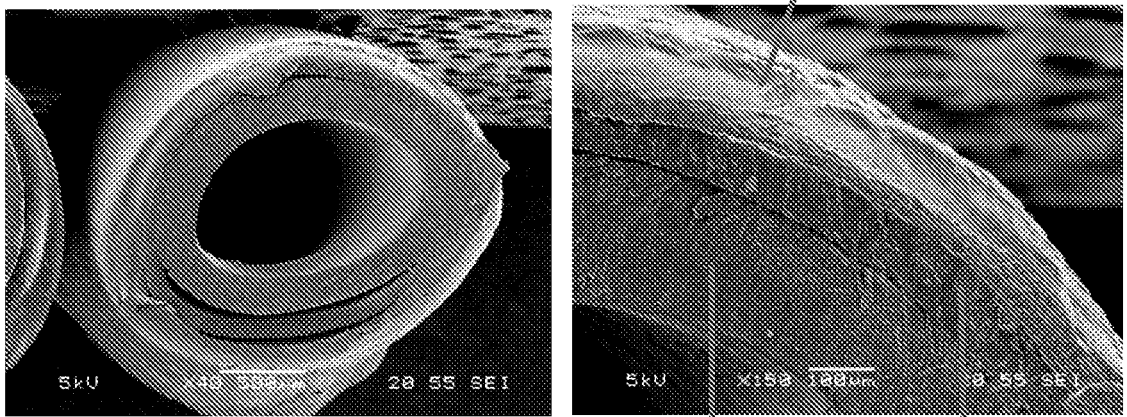
PEGDA (dry)
PU stent    PLC with MMC (A)

(B)

FIG. 13
(A)
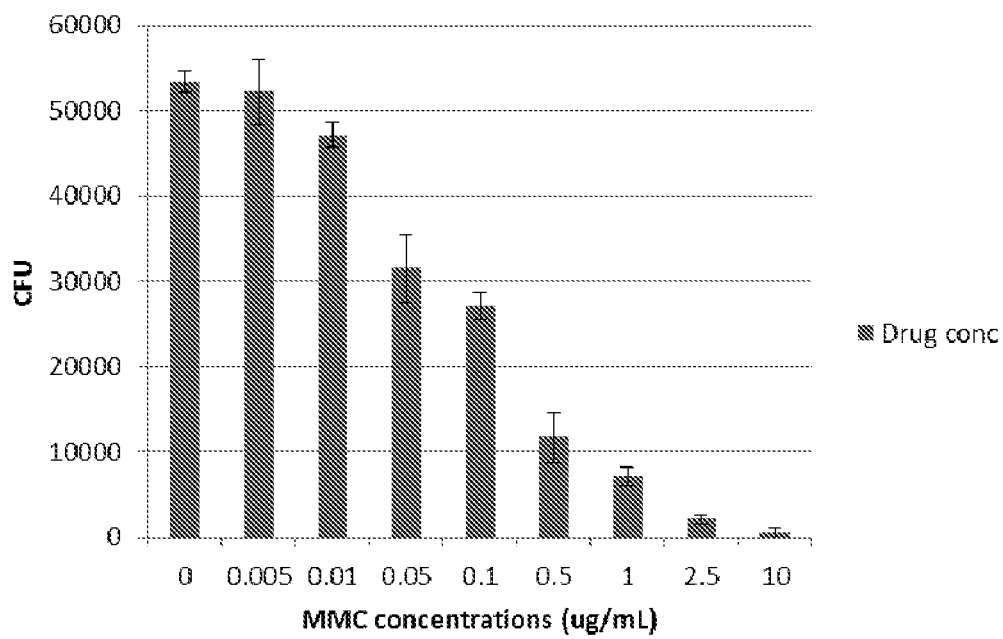
(B)
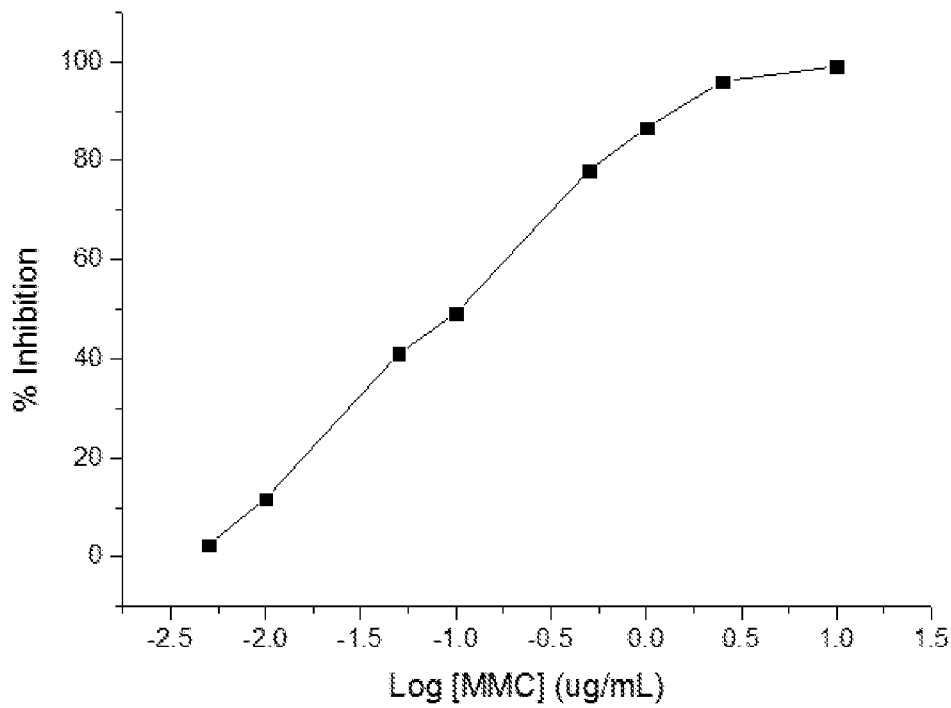

FIG. 14
(A)
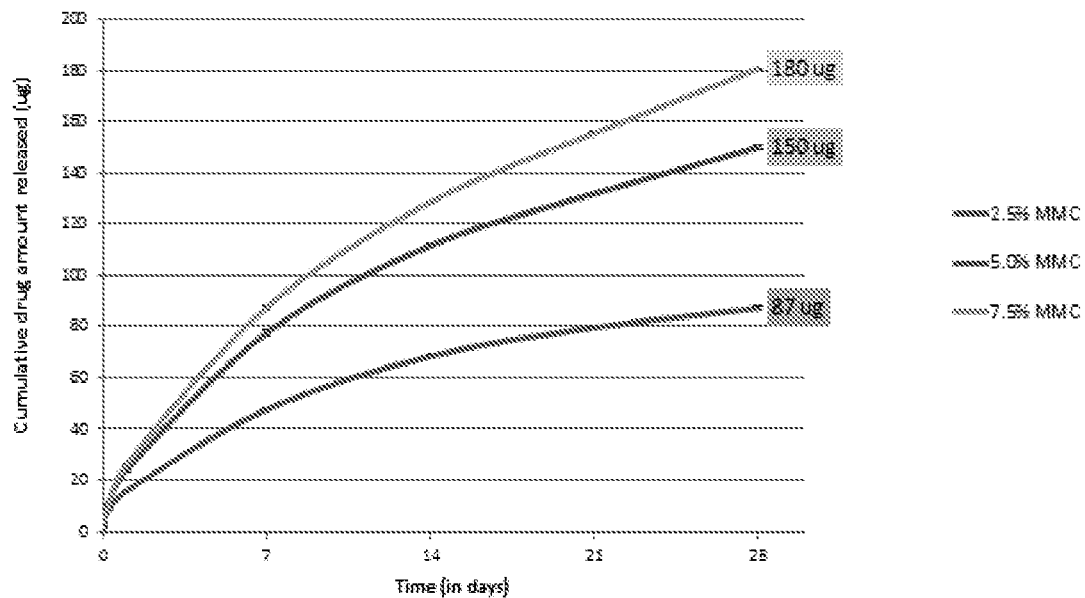
(B)
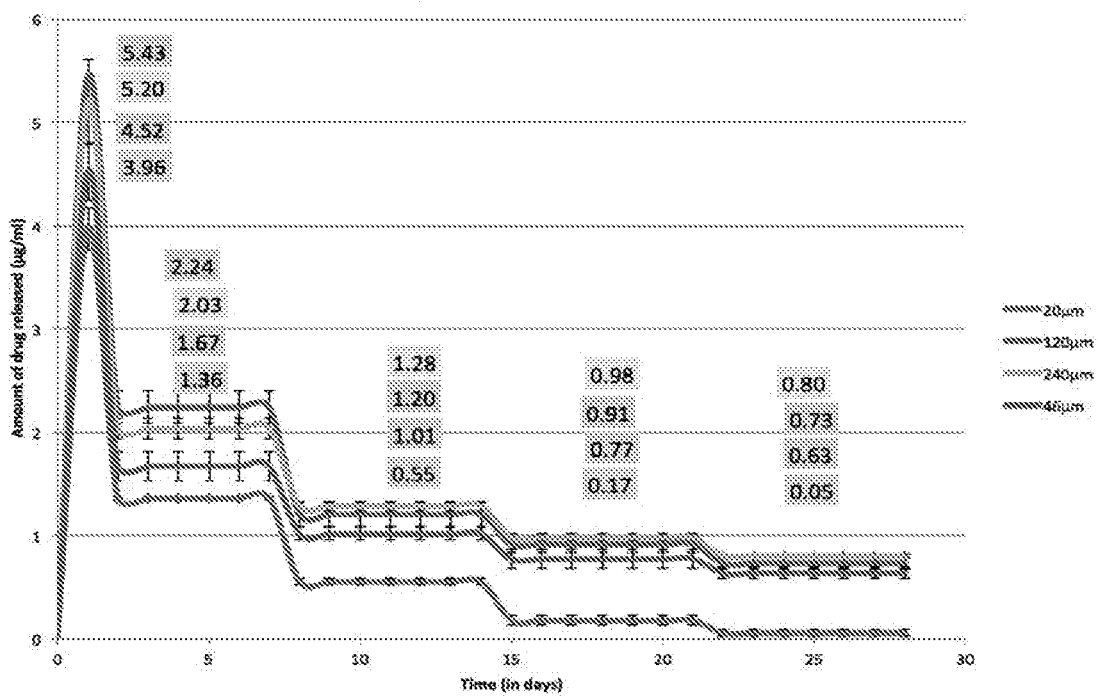

FIG. 14 (Cont.)
(C)
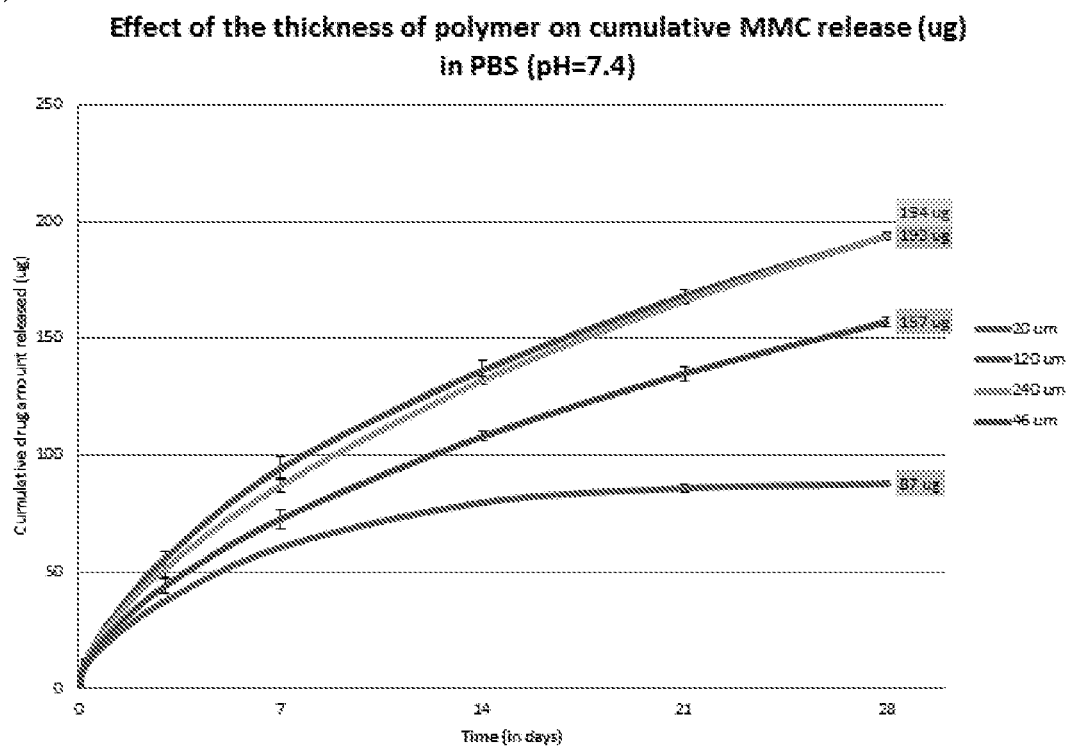
(D)
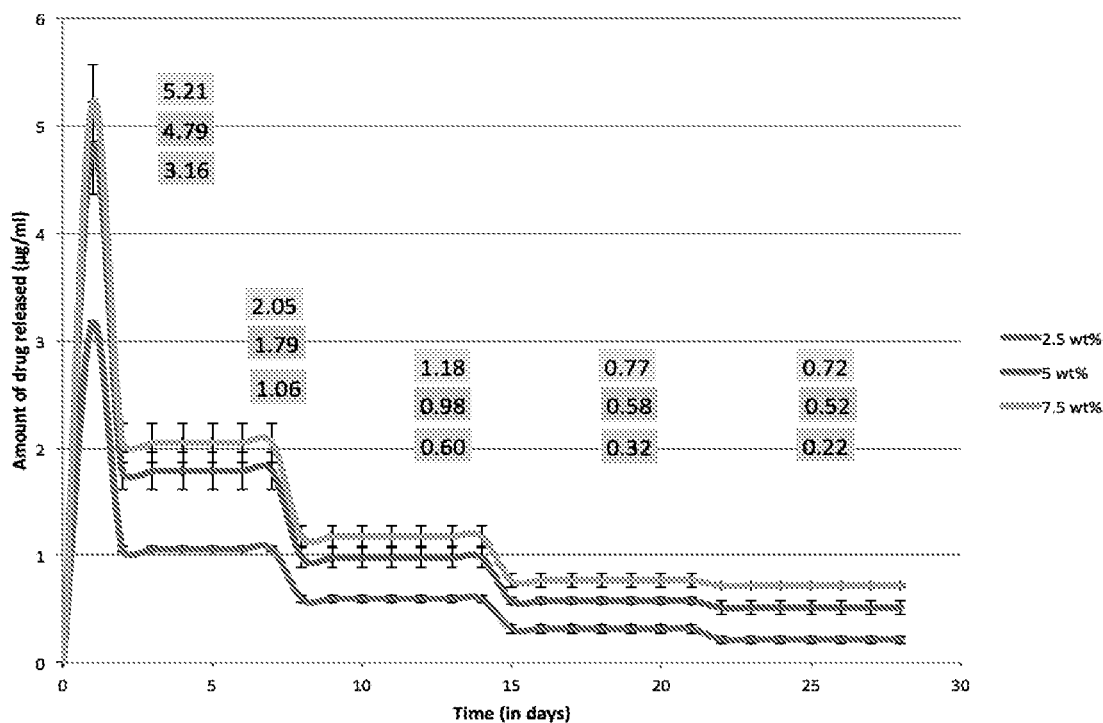

FIG. 15
(A)
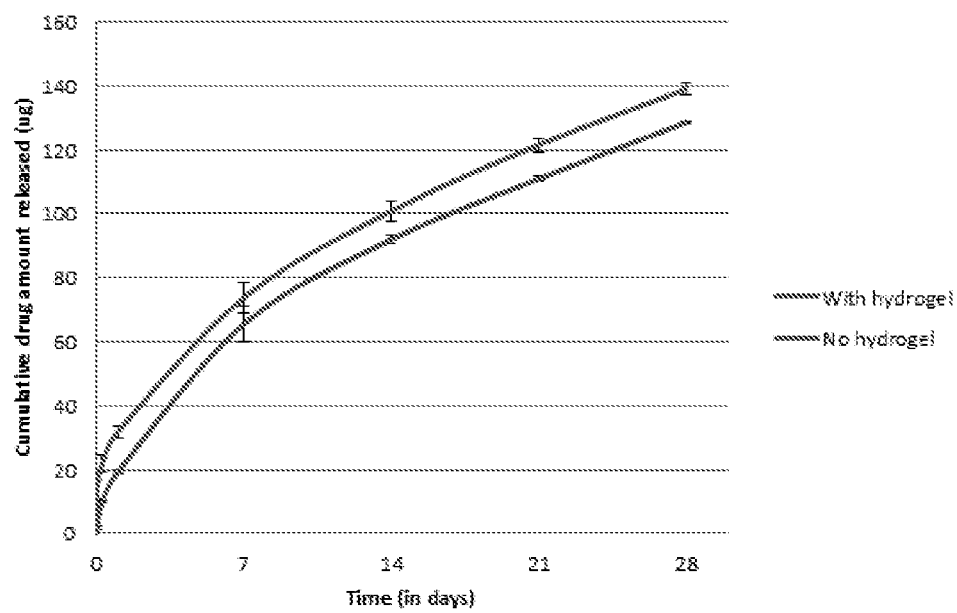
(B)
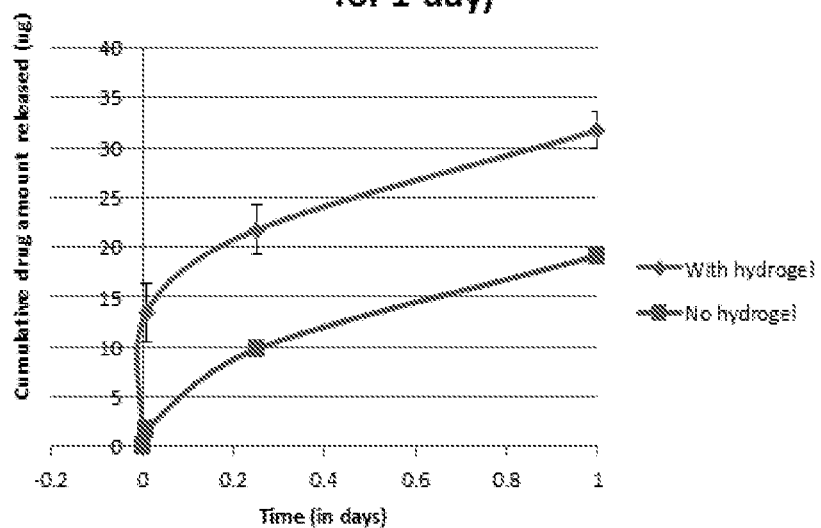

FIG. 18
(A)
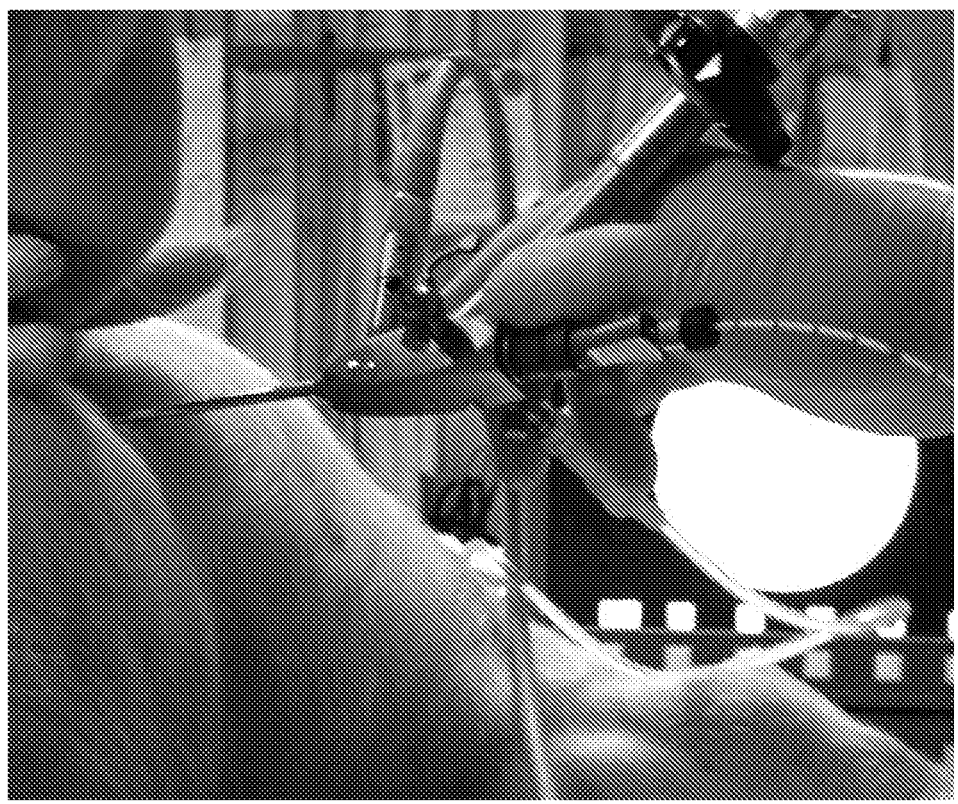
(B)
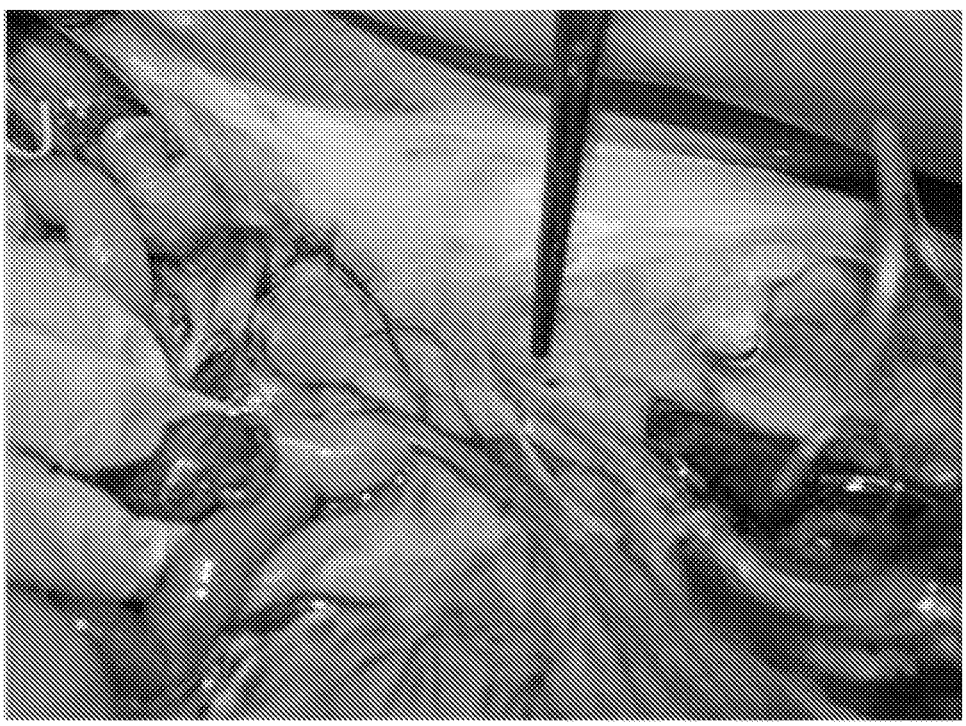

FIG. 18 (Cont.)
(C)
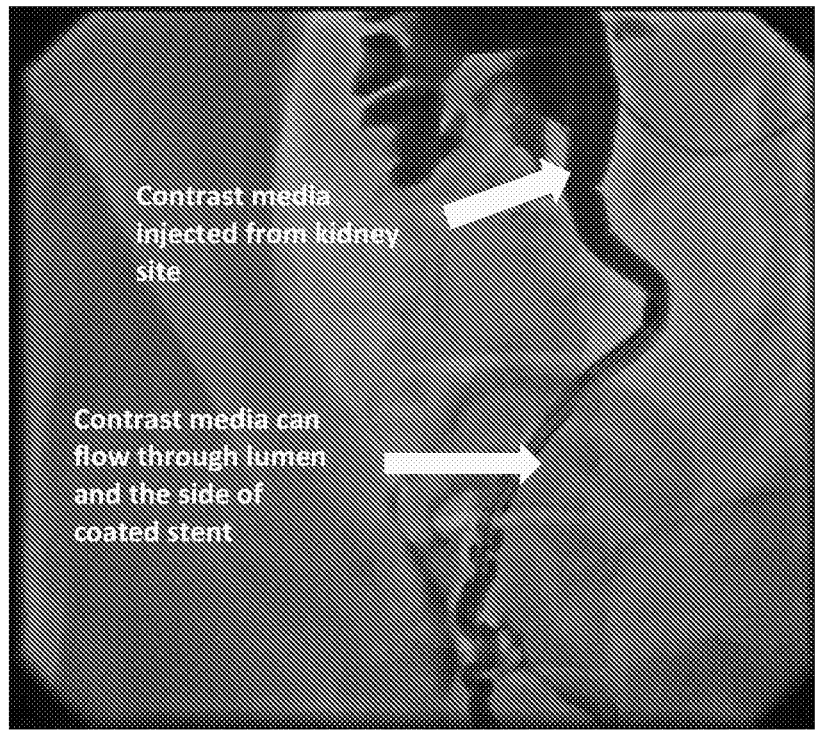
(D)
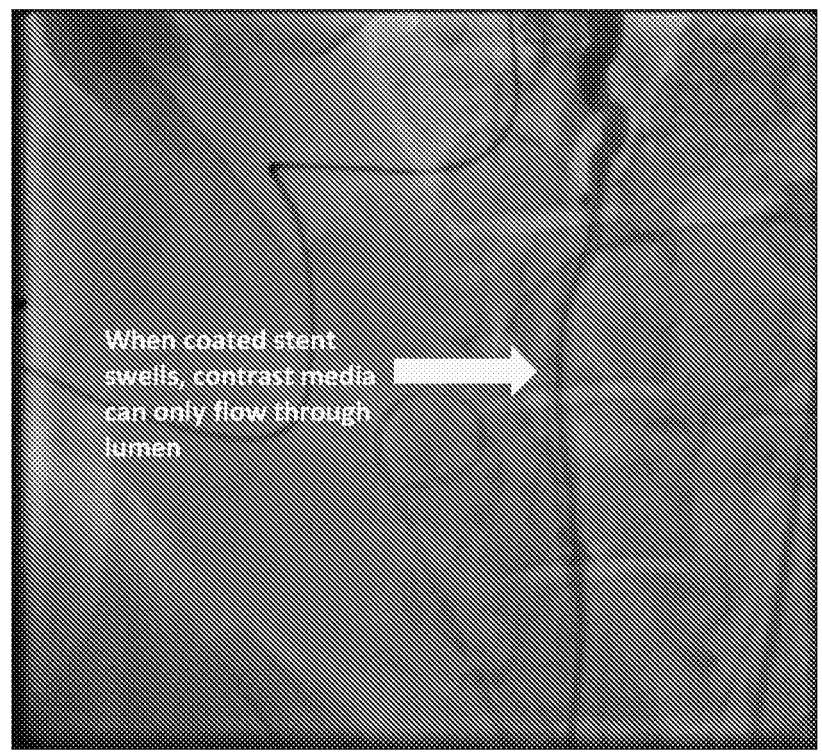

(E)

STENT ASSEMBLY AND METHOD OF PREPARING THE STENT ASSEMBLY

CROSS-REFERENCE TO RELATED APPLICATION

This application claims the benefit of priority of Singapore patent application No. 10201502162X filed on 19 Mar. 2015, the content of which is incorporated herein by reference in its entirety for all purposes.

TECHNICAL FIELD

Various embodiments relate generally to stents, more particularly, to ureteral stents with drug elution capabilities.

BACKGROUND

Stents with drug elution capabilities may address problems associated with coronary or peripheral vascular blockages, or ureteral strictures. Conventionally, the drug is contained in a polymer coating which covers the stent and may be released from this polymer coating after the stent has been placed into the subject to be treated. The drug-containing coatings, however, are liable to delaminations, especially during stent expansion. In such instances, the drug cannot be delivered to the desired location or in the desired amount. Therefore, it is important for such drug containing coatings to be able to maintain their mechanical integrity during storage and especially after stent expansion using a balloon.

In this connection, a few types of drug eluting stent have been tested in the ureteric track. Ureteral stents have been used to create a pathway for urinary drainage from the kidney to the bladder in patients with ureteral strictures, obstruction, and injury or to protect the integrity of the ureter in a variety of surgical procedure, among other uses. A number of clinical conditions may produce interruption in urine flow including, for example, intrinsic obstruction of the ureter due to stricture, tumor growth or stones, compression of the ureter due to extrinsic tumor growth, stone fragment impaction in the ureter following extracorporeal shock wave lithotripsy (ESWL), and ureteroscopy or endopyelotomy. Stents may thus be used to treat or prevent obstructions of the ureter that disrupt the flow of urine from the corresponding kidney to the urinary bladder, which obstructions can cause urine to back up into the kidney, threatening renal function.

Moreover, ureteric strictures are an important urological problem that may potentially lead to much morbidity and loss of a functioning kidney. Ureteric strictures may result from a variety of causes, including stone passage, endoscopic urologic procedures, radiation therapy, open or laparoscopic surgery, and penetrating traumatic injuries. Treatment involves full thickness endoscopic incision of the ureteric stricture, deliberately causing a controlled perforation and dilation of the lumen, followed by healing over an indwelling ureteric stent in 6 weeks. The stents are removed at 6 weeks post incision. Depending on the length and severity of the original stricture, recurrences may occur and are treated with repeated endoscopic incisions albeit with diminishing success. Not uncommonly, failure of repeated endoscopic treatment results in open surgical repair of the diseased segment, or even in removal of the ipsilateral kidney following significant renal loss. The morbidity of ureteric strictures is therefore not insignificant.

To reduce stent related pain, a Ketorolac (an NSAID) loaded stent was investigated in a randomised study involving 276 patients. A trend towards treatment benefit was demonstrated. This stent was specially produced to incorporate the drug into the stent material (Boston Scientific Lexington™ stent).

In other cases, use of drug-eluting stents (DES) containing paclitaxel to prevent stenosis has been investigated in the ureter of a porcine model. In this context, a mesh type stent was employed to reduce the hyperplastic reaction of the urothelium in response to the stent itself. The use of mesh stents in urology, however, has not gained wide acceptance, principally because of difficulties in removing the mesh without further traumatising the urothelium. Use of mesh stents may therefore be more suited to situations requiring more permanent ureteric stenting, such as malignant ureteric obstruction. Stents loaded with antimicrobials (Triclosan) left indwelling for up to 3 months have been tested in an attempt to reduce stent related infection. Although the treated group experienced fewer symptomatic infections, a clinical benefit in terms of urine and stent cultures was not demonstrated.

In view of the above, there exists a need for an improved stent which overcomes or at least alleviates one or more of the above-mentioned problems.

SUMMARY

In a first aspect, a stent assembly is provided. The stent assembly comprises
  a) a stent;
  b) a swellable coating disposed on at least a portion of an exterior surface of the stent;
  c) optionally, a carrier dispersed in the swellable coating and/or disposed on at least a portion of an exterior surface of the stent; and
  d) an active agent comprised in at least one of the swellable coating or the carrier, if present.

In a second aspect, use of a stent assembly according to the first aspect as a ureteric stent is provided.

In a third aspect, a method of preparing a stent assembly is provided. The method comprises
  a) providing a stent,
  b) disposing a swellable material on the stent, optionally comprising dispersing a carrier in the swellable material and/or disposing a carrier on at least a portion of an exterior surface of the stent, and incorporating an active agent in at least one of the swellable material or the carrier, if present, to form a swellable coating on at least a portion of an exterior surface of the stent.

BRIEF DESCRIPTION OF THE DRAWINGS

The invention will be better understood with reference to the detailed description when considered in conjunction with the non-limiting examples and the accompanying drawings, in which:

FIG. 10(A) and FIG. 10(B) show a 2.5 cm cut section of a ureteral stent coated with 2 cm of polymer/drugs and 2 cm of hydrogel, while FIG. 10(C) and FIG. 10(D) show the full stent coated with the bilayer coating. FIG. 10(A) and FIG. 10(C) show the coating before swelling, whereas FIG. 10(B) and FIG. 10(D) show the coating after swelling. This demonstrates the technical feasibility of fabricating the coated stent.

FIG. 11(A) to (C) are SEM images showing the stent coated with polymer loaded with drugs (MMC) and without hydrogel polyethylene(glycol) diacrylate (PEGDA) for (A) 2.5% MMC; (B) 5% MMC; and (C) 7.5% MMC. FIG. 11(D) is a SEM image showing the stent coated with polymer (with drugs) of 5% MMC and hydrogel PEGDA. The stent used in the figures is a polyurethane (PU) stent. Surface morphology is shown to be smooth without any drug agglomerating.

TABLE 1

|  | 5% PEGDA | 7.5% PEGDA | 10% PEGDA |
| --- | --- | --- | --- |
| Initial thickness of PEGDA | 110 um | 155 um | 225 um |
| Time taken for coated section to swell to 4 mm (static model) | 1 h | 30 min | 30 min |
| Amount required to swell to reach ureteric diameter (4 mm) | 959% | 652% | 418% |

FIGS. 13(A) and (B) are graphs showing (A) relative cell count vs MMC concentrations (μg/mL), and (B) dose-response curve.

FIG. 14(A) to (D) depict graphs showing in vitro release studies of MMC from both polymer coated stent with different coating thickness and swellable bilayer coated stent in phosphate-buffered saline (PBS) having a pH of 7.4. The release profile were manipulated by thickness of polymer (20 μm, 120 μm, 240 μm, and 46 μm) and the drug loading (2.5% MMC, 5.0% MMC, and 7.5% MMC), to achieve about a wide array of drug amount, at around 90-200 μg cumulative MMC release over 28 days; and the daily drug dosage are above the minimum drug concentration of 0.01 μg/mL, to inhibit the fibroblast proliferation.

FIGS. 15(A) and (B) are graphs showing (A) effects of hydrogel coating on cumulative MMC release (μg) in PBS (pH=7.4); and (B) effects of hydrogel coating (zoomed in for 1-day). When used in vitro, the hydrogel coating did not have a significant effect on the drug release profiles. In the first few hours, there was a slightly higher amount of drug released for the samples coated with the hydrogel coating. This was likely due to the earlier onset of drug release for the samples with the hydrogel. During the drying step, the drug layer was still exposed to the aqueous hydrogel layer and had started to release drugs into the hydrogel. The drugs stored in the hydrogel were then released upon contact of the hydrogel with water where the hydrogel started to swell.

However, in vivo, the swellable hydrogel was able to act as a bridge to enhance or delivery the drug to ureteric tissue. A slightly higher drug amount was released initially when hydrogel was present.

Figure 16:
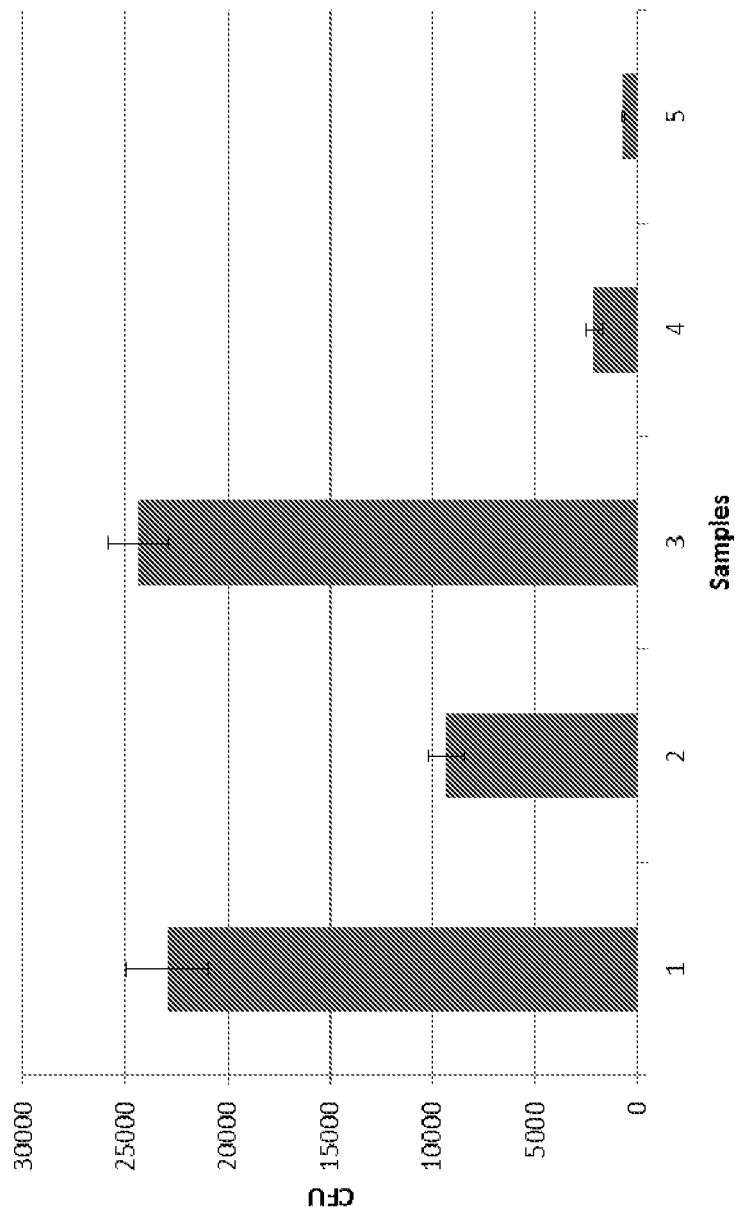

FIG. 16 is a graph showing effect of MMC-eluting ureteral stents on fibroblast inhibition for Sample 1: No drugs, no stent; Sample 2: 0.5 ug/mL MMC; Sample 3: Stent/PLC/PEGDA; Sample 4: Stent/PLC/MMC (5%); and Sample 5: Stent/PLC/MMC (5%)/PEGDA.

FIGS. 17(A) and (B) are photographs showing tapered ends of an embodiment of a stent disclosed herein. A tapered end design was applied to the coating to address and/or alleviate problems associated with stent removability upon swelling of the coating.

FIG. 18(A) to (E) are photographs showing (A) the coated stent may be inserted through the adult cystoscope (22 F, 40 cm) into the pig ureter; (B) a coated stent is placed in the ureter from an incision made from the kidney; (C) the contrast was injected from the proximal end (kidney site), the X-ray images shows the stent in correct position of ureteric tract. Before the gel swells, the contrast media is able to run through the inner lumen of the stent and the sides (gap between stent surface and urothelial tissues); and (D) the coated stent was left in the ureter for 35 mins to allow for swelling. The contrast media was injected and it is observed that the media is able to run through inner lumen of stent, but not the sides, this demonstrated the present hydrogel is able to swell and contacted with the urothelial tissues in 35 mins in vivo; (E) the stent was removed easily and successfully. The final swollen diameter was measured at 4 mm, comparable to ureteric diameter. This demonstrates that the stent may be easily inserted and removed from the ureter, and also that the coating section on the stent was able to swell in the porcine ureter.

DETAILED DESCRIPTION

In a first aspect, a stent assembly is provided. The stent assembly disclosed herein is able to inhibit ureteral fibroblast proliferation so as to prevent stricture recurrence. By incorporating a swellable coating on at least a portion of an exterior surface of a stent, the swellable coating is able to swell up to 1500 times its volume when in contact with a medium. Under urinary conditions, for example, the ureteric stent may swell towards and/or be in contact with ureter wall to enhance localized drug delivery. As the swellable coating may be applied on an existing conventional stent, this provides greater ease of acceptance by patients and practitioners since the protocols at which the stents are used may remain unchanged. Advantageously, the stent assembly provides greater versatility in use, since, depending on where the active agent is located, active agent may be dispensed from the stent assembly in a quick release form (when it is incorporated in the swellable coating), or in a controlled release form (when it is incorporated in the carrier).

The stent assembly disclosed herein comprises a stent. The term "stent" as used herein refers to a prosthesis, usually a thin tube which may be in the form of a slotted tube, a helical coil, or a wire mesh tube, designed to be inserted into a vessel or passageway of a subject (usually a mammal such a human, dog, mouse, rat, etc) to be treated to keep it open.

Figure 1:
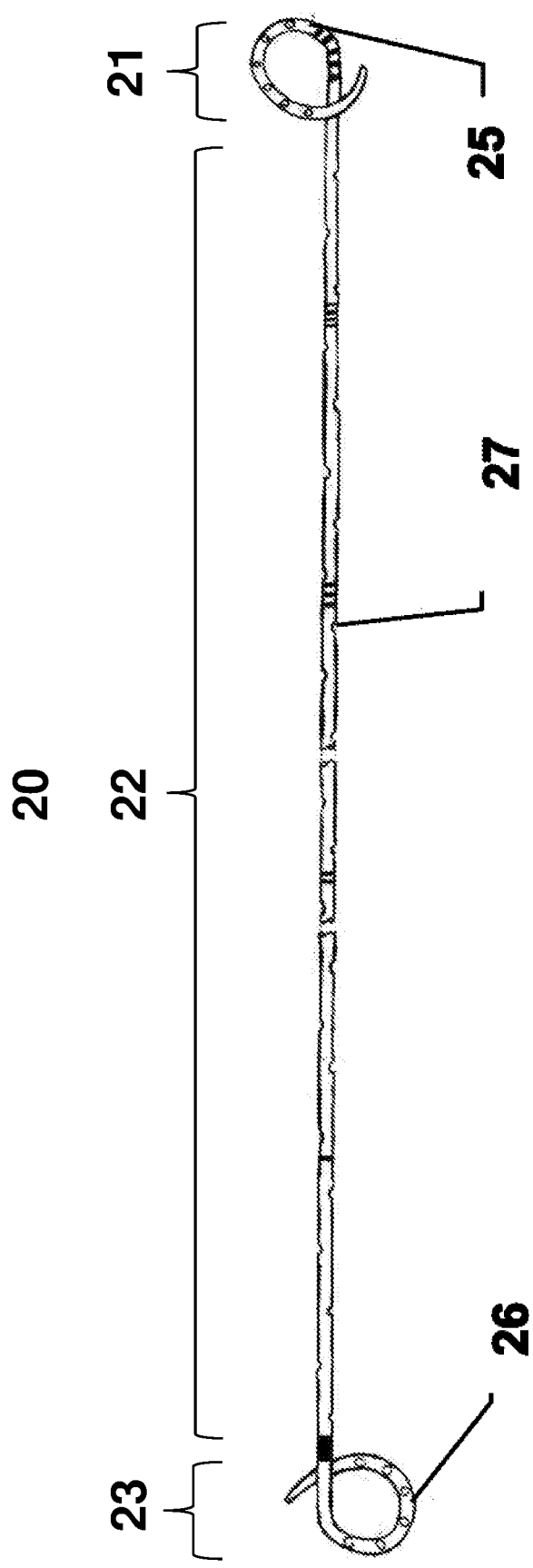
FIG. 1 shows a ureteric stent (20) having a proximal portion (21), a central portion (22) and a distal portion (23) according to an embodiment. Small holes (27) are present in the ureteric stent (20). A proximal retention structure (25) configured for retaining the proximal portion (21) in the urinary bladder, and a distal retention structure (26) configured for retaining the distal portion (23) in the renal pelvis of kidney are also shown.

In specific embodiments, the stent is a ureteric stent. A ureteric stent refers generally to a drainage device that facilitates drainage of urine from the kidney through the ureter and into the urinary bladder. The stent may be tubular in shape, terminating in two opposing ends: a distal (kidney) end and a proximal (urinary bladder) end. One or both of the ends of the stent may have a retention structure, such as that shown in FIG. 1.

Figure 2:
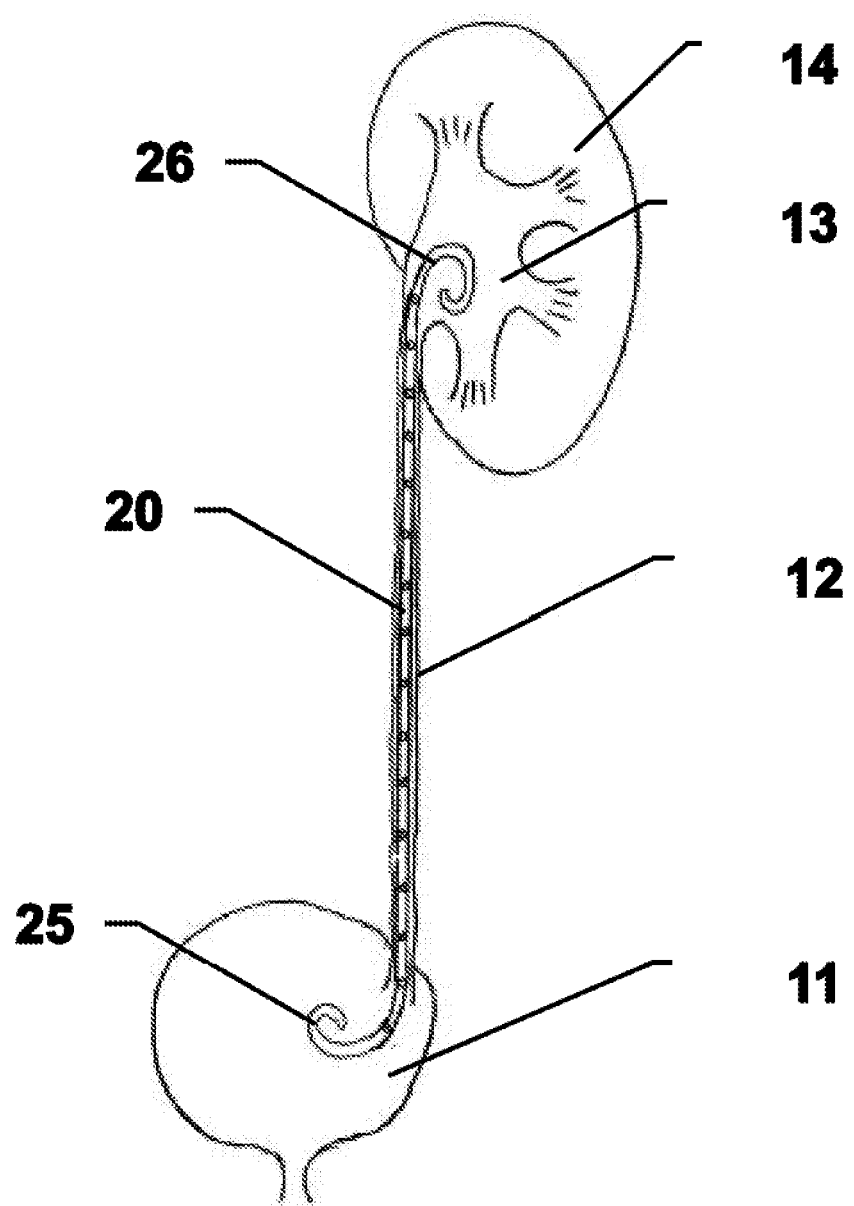
FIG. 2 shows a ureteric stent (20) depicted in FIG. 1 as positioned within a human body. A proximal retention structure (25) configured for retaining the proximal portion in the urinary bladder (11), a central portion configured to fit the ureter (12) of a human patient, and a distal retention structure (26) configured to stay in the renal pelvis (13) of kidney (14) and prevent stent migration are shown.

A distal (kidney) retention structure is designed to retain the distal end of the stent within the renal pelvis and to prevent stent migration down the ureter toward the urinary bladder, such as that shown in FIG. 2. A proximal (urinary bladder) retention structure, on the other hand, is designed to retain the proximal end of the stent within the urinary bladder and to prevent stent migration up the ureter toward the kidney, such as that shown in FIG. 2.

The ureteric stent disclosed herein may be designed to be inserted into the ureter to create a pathway for urinary drainage from the kidney to the bladder in patients with ureteral strictures, obstruction, and injury or to protect the integrity of the ureter in a variety of surgical procedure. When used for this purpose, the stent then allows the normal flow of urine from kidney. Accordingly, the stent may have a hollow cylindrical configuration. The stent may have any suitable size defined in terms of length, outer diameter and wall thickness, for example, for application as a ureteric stent.

Figure 17:
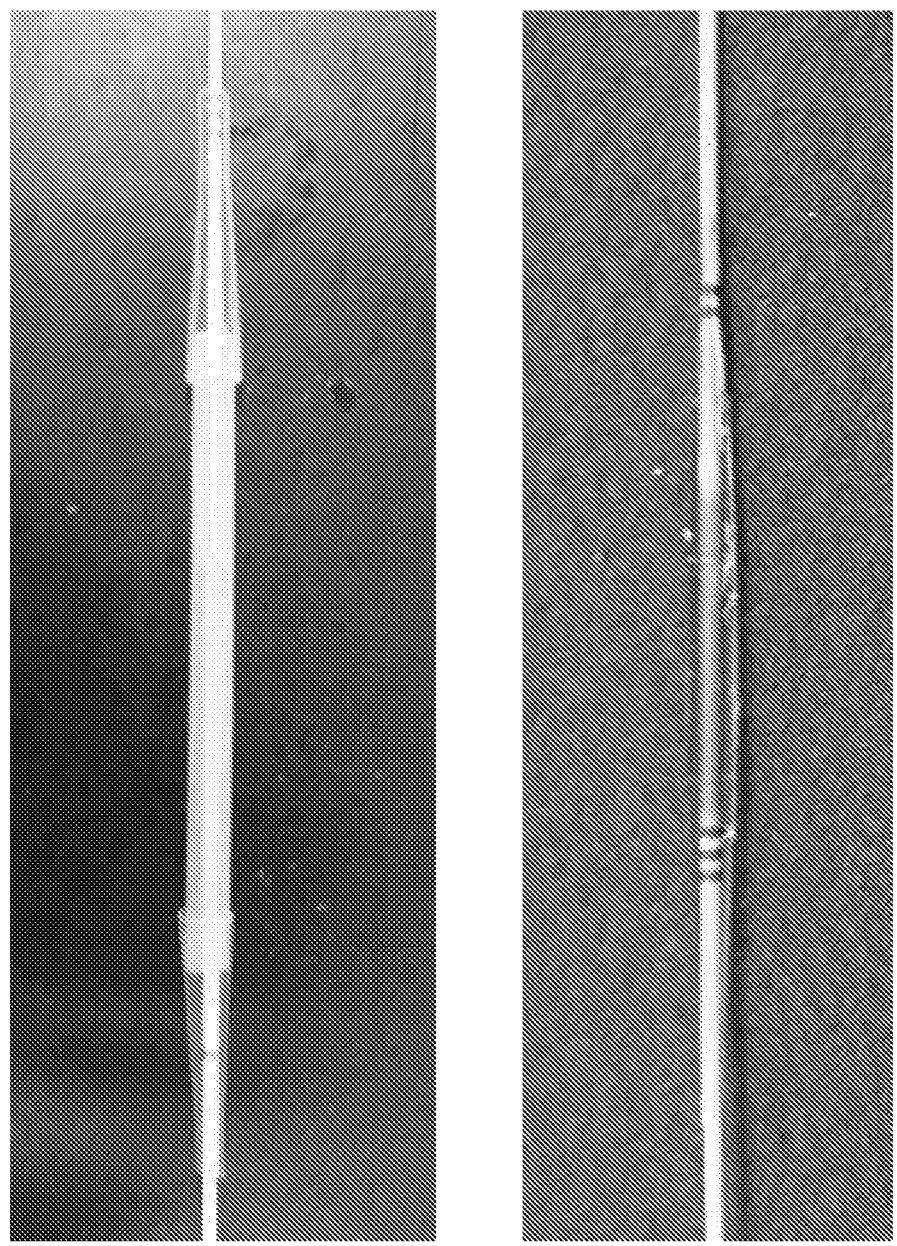
Figure 18:
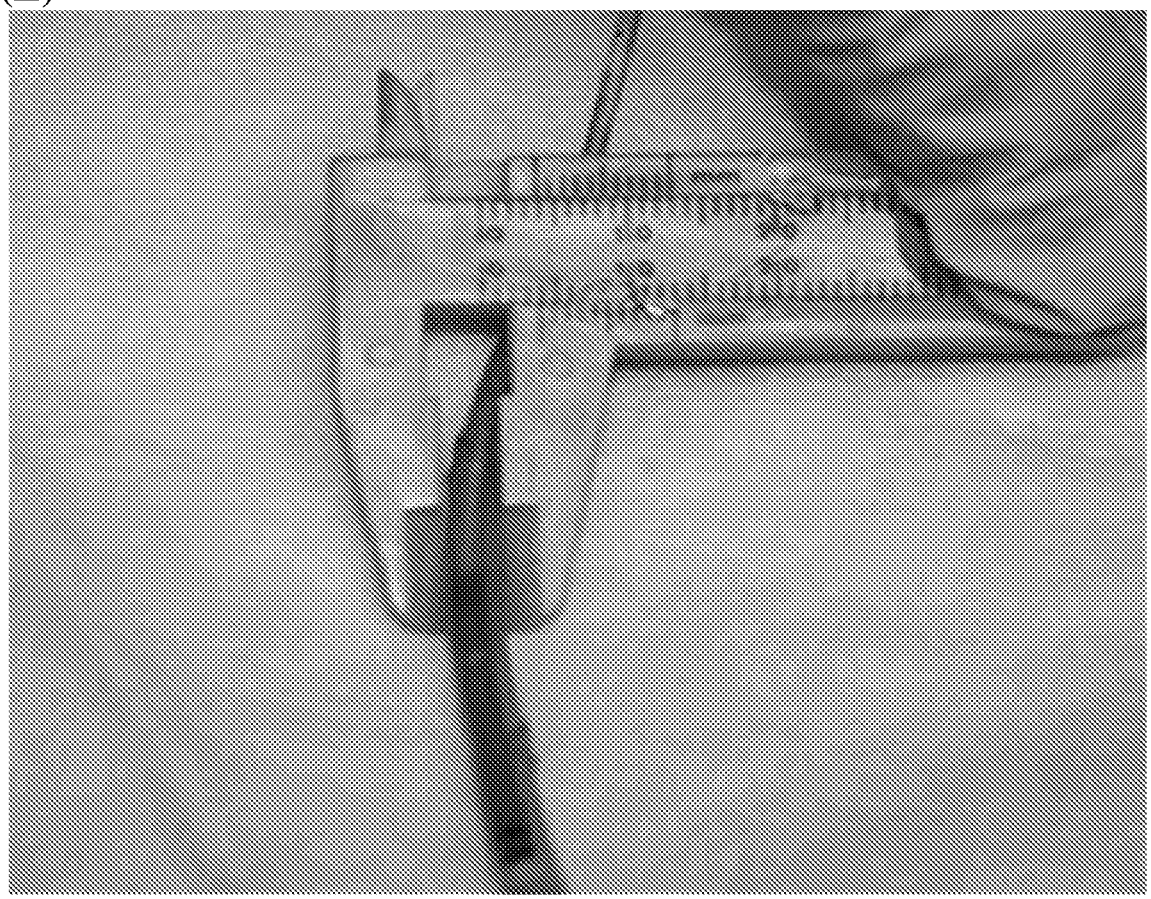

In some embodiments, the stent comprises tapered ends, such as that shown in FIG. 17. A tapered end design may be applied to the stent to address and/or to alleviate problems associated with stent removability upon swelling of the coating.

Though designed for such functions, a stent disclosed herein may also be used in other applications or other body parts such as, but not limited to, the esophagus to treat a constriction, or bile duct to keep it open.

In various embodiments, the stent comprises a material selected from the group consisting of a thermoplastic polymer, an elastomeric polymer, a thermoplastic elastomer, copolymers thereof, and combinations thereof, which may, for example, be used to form the stent body and retention structures.

In various embodiments, the stent may comprise or consist of polycarboxylic acid polymers and copolymers including polyacrylic acids; acetal polymers and copolymers; acrylate and methacrylate polymers and copolymers (e.g., n-butyl methacrylate); cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e. g., Pebax® resins), polycaprolactams and polyacrylamides; polycarbonates; polyacrylonitriles; polyvinylpyrrolidones; polymers and copolymers of vinyl monomers including polyvinyl alcohols, polyvinylhalides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and mesolactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one; polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene),ethylene propylene diene monomer (EPDM) rubbers, poly 4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers; as well as blends and further copolymers of the above, polyurethanes (polyester polyurethanes, polyether polyurethanes, polycarbonate polyurethanes polyolefin polyurethanes, etc.), polyether-block-polyamide copolymers (e.g., poly[tetramethylene oxide]b-polyamide-12 block copolymer, available from Elf Atochem as PEBAX), polycarbonates (e.g., bisphenol A polycarbonate), silicones (e.g., siloxanes such as polydimethylsiloxane, polydiethylsiloxane, polymethylethylsiloxane, polymethylphenylsiloxane, and polydiphenylsiloxane, etc., which are commonly covalently crosslinked), polytetrafluoroethylene, and ethylene copolymers such as ethylene-vinyl acetate copolymers (EVA), among others.

A swellable coating is disposed on at least a portion of an exterior surface of the stent. As used herein, the term "swellable coating" refers to a coating formed of a swellable material, for example, a material that is able to swell or increase in volume in the presence of a liquid such as an aqueous medium. The terms "aqueous medium" and "aqueous solution" as used herein are used interchangeably, and refers to water or a solution based primarily on water such as phosphate buffered saline (PBS), or water containing a salt dissolved therein.

For example, the swellable material may absorb the liquid to result in the swelling or increase in volume. The swellable coating as disclosed herein may swell up to 1500 times its volume. In various embodiments, the swellable coating is adapted to swell by about 5 times to about 160 times its volume.

Materials for forming the swellable coating may possess properties of absorbing and releasing a large amount of the liquid medium, thereby exhibiting transport properties like in a fluid. Suitable materials that may be used for forming the swellable coating may include water swellable polymers or superabsorbent polymers, which may swell in the presence of a liquid such as an aqueous medium. The water swellable polymers or superabsorbent polymers may in some embodiments be classified as a hydrogel when cross-linked.

In various embodiments, the swellable coating comprises a swellable material selected from the group consisting of a hydrogel, a water swellable polymer, a superabsorbent polymer, copolymers thereof, and combinations thereof.

In specific embodiments, the swellable coating comprises or consists of a hydrogel.

As disclosed herein, the term "hydrogel" refers to a broad class of polymeric materials, that may be natural or synthetic, which have an affinity for an aqueous medium, and may absorb large amounts of the aqueous medium, but which do not normally dissolve in the aqueous medium.

A hydrogel may generally be formed by using at least one, or one or more types of hydrogel-forming agent, and setting or solidifying the one or more types of hydrogel-forming agent in an aqueous medium to form a three-dimensional network, wherein formation of the three-dimensional network may cause the one or more types of hydrogel-forming agent to gel so as to form the hydrogel. The term "hydrogel-forming agent", also termed herein as "hydrogel precursor", refers to any chemical compound that may be used to make a hydrogel. The hydrogel-forming agent may comprise physically cross-linkable or chemically cross-linkable monomers, homopolymers, copolymers, or mixtures thereof.

The swellable coating comprising hydrogel may be formed by applying a hydrogel-forming agent to the stent surface in solution, followed by cross-linking to obtain the swellable coating. Total absorbency and swelling capacity may be controlled by the type and degree of cross-linking in the hydrogel. Low-density cross-linked hydrogel may generally have a higher absorbent capacity and swell to a larger degree, while high-density cross-linked hydrogels may exhibit lower absorbent capacity and swell to a lesser degree. Due to formation of a cross-linked network structure via covalent or non-covalent bonds, the hydrogel, which may generally be composed of hydrophilic organic polymers, may be structurally stable.

Examples of suitable hydrogels which may be used include a hydrogel made from hydrogel-forming agents such as polyvinyl alcohol, polyglycols such as polyethylene glycol dimethacrylate, polyethylene glycol diacrylate, acrylamide, polyacrylic acid, hydrolyzed polyacrylonitrile, polyethyleneimine, ethoxylated polyethyleneimine polyallylamine, and polyglycols, anionic polymers such as hyaluronic acid, methacrylated hyaluronic acid (HAMA), cationic polymers such as chitosan, amphipathic polymers such as collagen, gelatin and fibrin, neutral polymers such as dextran and agarose, as well as monomers of the aforementioned, oligomers of the aforementioned, macromers of the aforementioned, copolymers of the aforementioned, and/or derivatives of the aforementioned.

In some embodiments, the swellable coating comprises a hydrogel made from poly(ethylene glycol) diacrylate (PEGDA), methacrylated hyaluronic acid, or combinations thereof.

In addition to, or apart from the above-mentioned, interpenetrating polymer networks, which may be formed by various combinations of water soluble polymers and water insoluble precursors, and polymers having backbones modified with calcium or phosphate derivatives may also be suitable for use in certain embodiments.

Figure 3:
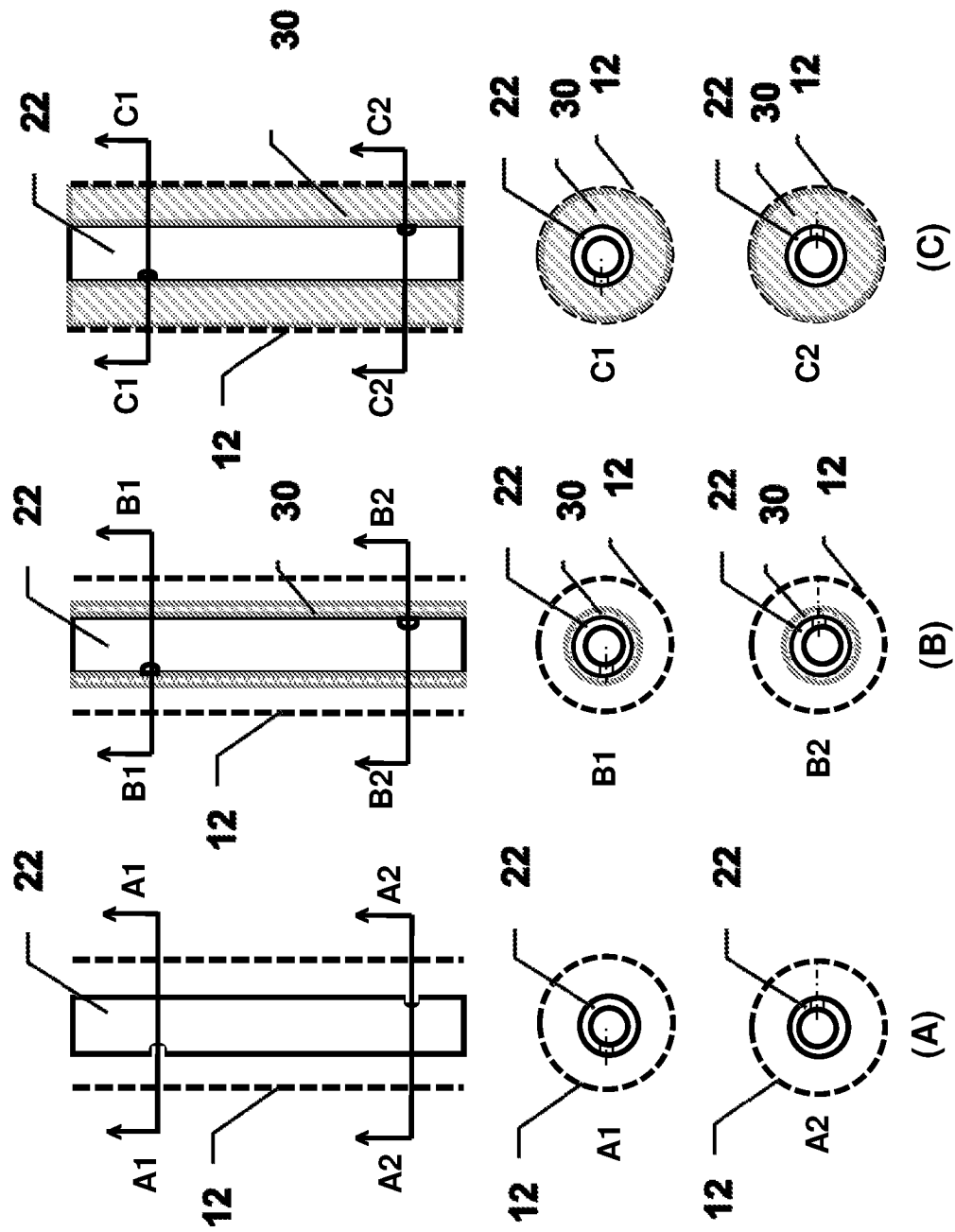
FIG. 3(A) shows a side view of a central portion (22) of a ureteral stent depicted in FIG. 1 and FIG. 2 as positioned in the ureter of a human body; A1 is a cross-sectional view of the stent illustrated in FIG. 3(A), taken along line A1-A1; A2 is a cross-sectional view of the stent illustrated in FIG. 3(A), taken along line A2-A2.
FIG. 3(B) shows a central portion (22) of a ureteral stent as depicted in FIG. 1 and FIG. 2 with a swellable coating (30) in an unswollen state according to an embodiment. B1 is a cross-sectional view of a stent illustrated in FIG. 3(B), taken along line B1-B1; B2 is a cross-sectional view of the stent illustrated in FIG. 3(B), taken along line B2-B2.
FIG. 3(C) shows a central portion (22) of a ureteral stent depicted in FIG. 1 and FIG. 2 with a swellable coating (30) in a swollen state and contacting with the ureter wall (12) in a specific embodiment. C1 is a cross-sectional view of a stent illustrated in FIG. 3(C), taken along line C1-C1; C2 is a cross-sectional view of the stent illustrated in FIG. 3(C), taken along line C2-C2.
Figure 4:
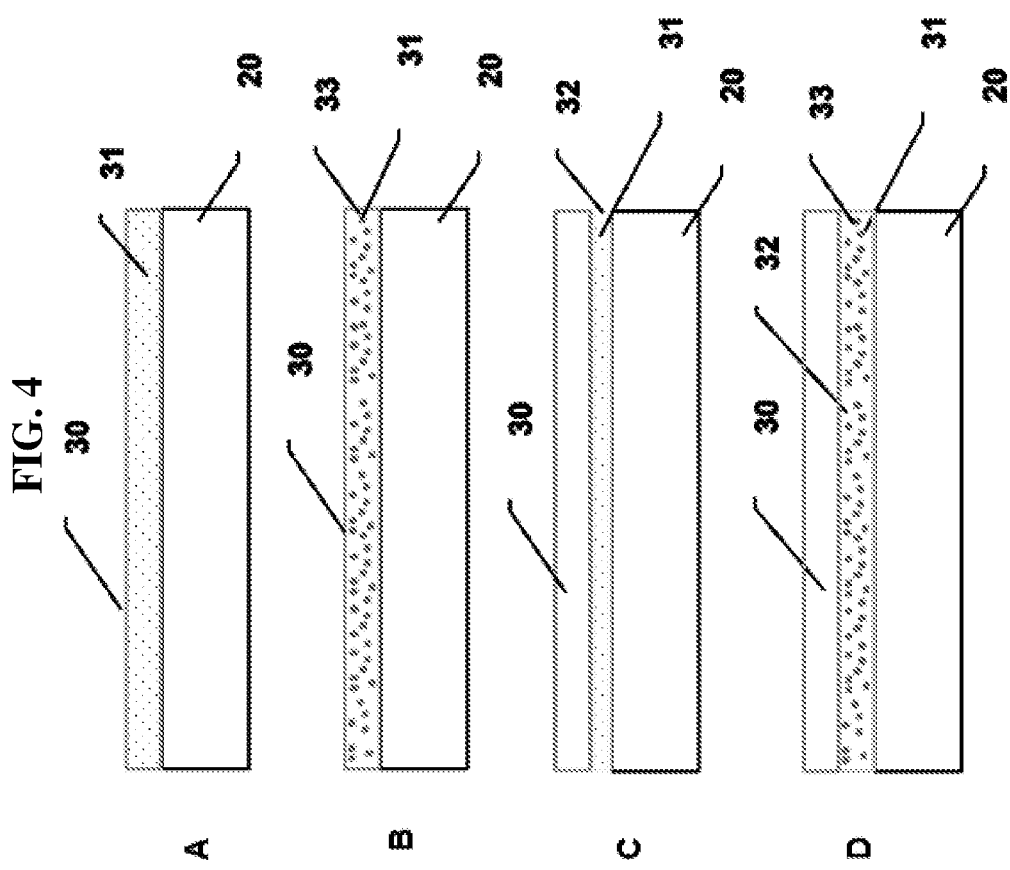
FIG. 4(A) is a partial view of a stent (20) according to an embodiment having a single swellable layer (30), with a urological beneficial agent (31).
FIG. 4(B) is a partial view of a stent (20) according to an embodiment disclosed herein having a single swellable layer (30) comprising the drug delivery platform in the form of nano-carriers (33) loaded with a urological beneficial agent (31).
FIG. 4(C) is a partial view of a stent (20) disclosed herein having a multiple layer structure of the coating which comprises a top swellable layer (30), and a drug delivery platform in the form of a layer (32) positioned between the swellable layer (30) and the stent (20) and which is loaded with a urological beneficial agent (31).
FIG. 4(D) is a partial view of a stent (20) to an embodiment having a multiple layer structure of the coating, which comprises a top swellable layer (30) and a first drug delivery platform in the form of a layer (32) positioned between the swellable layer (30) and the stent (20). The layer (32) contains a second drug delivery platform in the form of nano-carriers (33) loaded with a urological beneficial agent (31).
Figure 5:
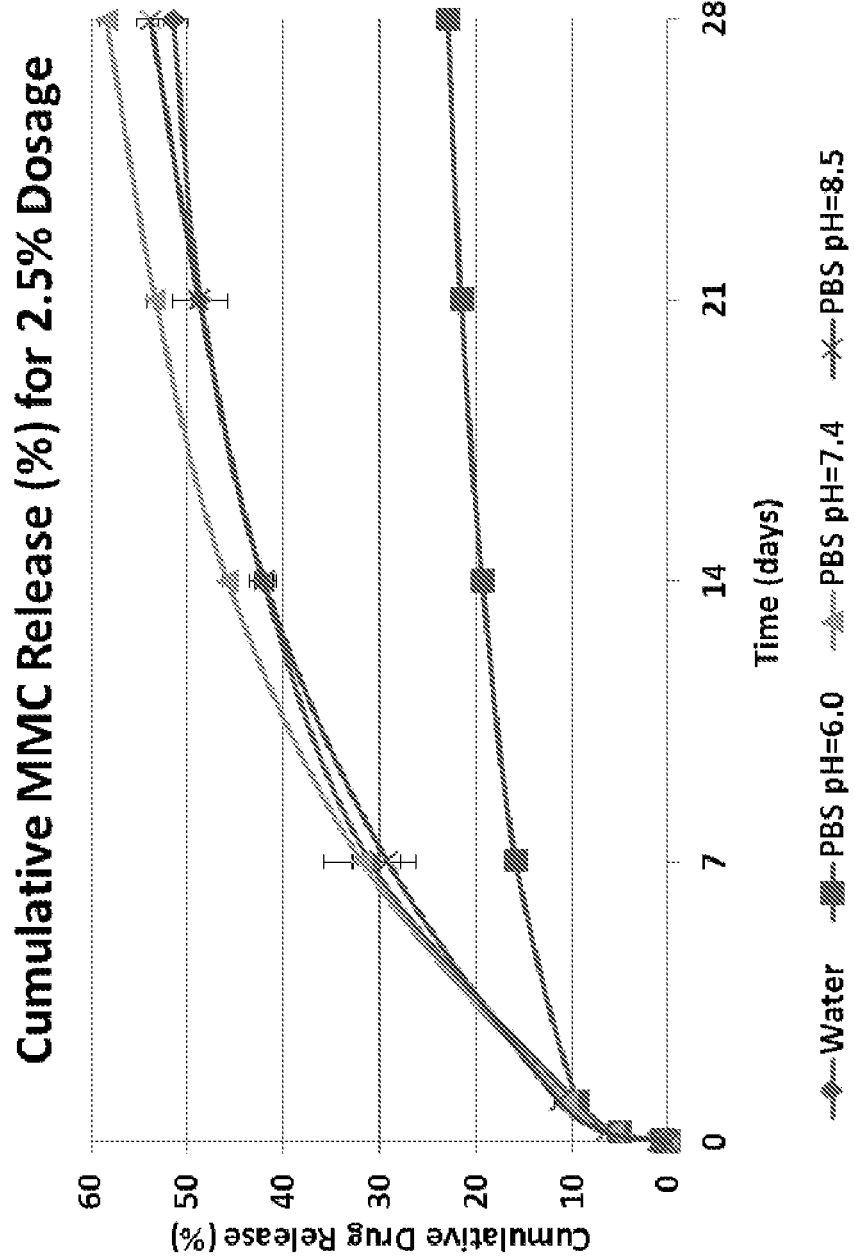
FIG. 5 is a graph showing cumulative mitomycin-C (MMC) (2.5% dosage) drug release profile from a bilayer coated stent of one embodiment at 37° C. in water, and buffer solution (pH=6.0, pH=7.4, and pH=8.5).
Figure 6:
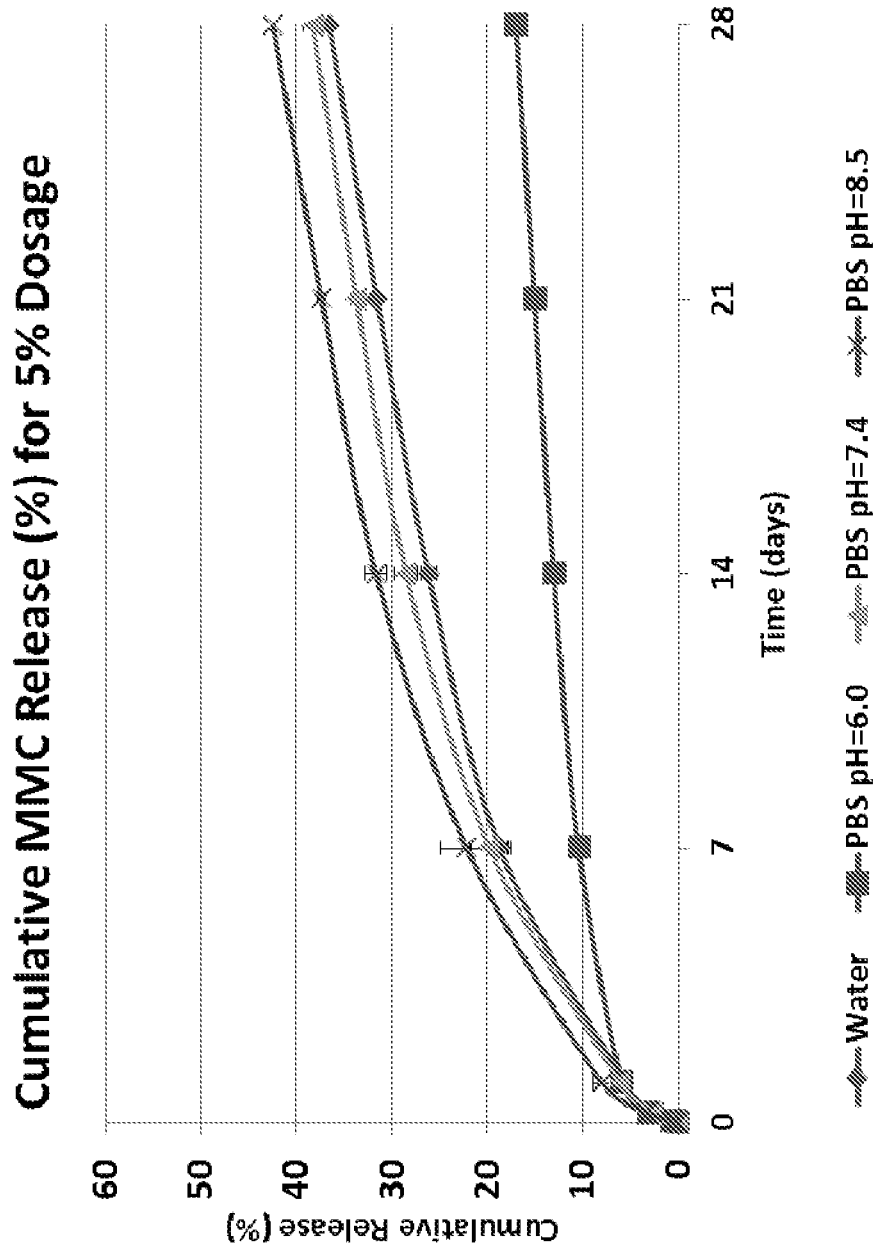
FIG. 6 is a graph showing cumulative mitomycin-C (MMC) (5% dosage) drug release profile from a bilayer coated stent of another embodiment at 37° C. in water, and buffer solution (pH=6.0, pH=7.4, and pH=8.5).

In some embodiments, such as that depicted in FIG. 3, the swellable coating, which is disposed on at least a portion of an exterior surface of the stent, swell towards and contacts with ureter wall in urinary condition. By virtue of the direct contact of the swellable coating with the ureter wall, this allows localized delivery of the active agent into a subject to take place. As used herein, the term "subject" generally refers to any host, animal, vertebrate, or invertebrate, and includes fish, mammals, amphibians, reptiles, birds, and particularly humans. In specific embodiments, such as that shown in FIG. 4, the active agent is loaded into the swellable coating directly to achieve fast release of the active agent to the intended delivery site.

As used herein, the term "active agent" refers generally to a molecule, a compound or a composition that elicits a biological response from a subject as defined above. For example, the active agent may be an agent providing some pharmacologic effect, often beneficial, and may in some embodiments be capable of treating, inhibiting, or preventing a disorder or a disease.

Examples of active agents include therapeutic agents, pharmaceutical agents, pharmaceuticals (such as a therapeutic compound, a pharmaceutical salt), non-pharmaceuticals (such as a cosmetic substance), a vaccine, an immunological agent, a local or general anesthetic or painkiller, an antigen or a protein or peptide such as insulin, a chemotherapy agent, or an anti-tumor agent, pharmacologically active salts of the active agents, pharmaceutically acceptable salts of the active agents, proactive agents of the active agents, metabolites, analogs, and the like.

In some embodiments, the active agent is selected from the group consisting of an antifibrotic agent, an anticancer agent, a discomfort reducing agent, an antibacterial agent, a gene, a gene vector, a growth factor, and combinations thereof.

The term "antifibrotic agent" refers to one or more chemical or biological compounds having antifibrotic activity in mammals. The compounds may have different mechanisms of action, for example, some may work by reducing formation of collagen or another protein, while others may work by enhancing metabolism or removal of collagen in the affected area of the body. All such compounds having activity in the reduction of the presence of fibrous tissue may be suitable for use as an antifibrotic agent disclosed herein, without regard to the particular mechanism of action by which the compound functions.

Specific examples of an antifibrotic agent include mitomycin-C, 5-Flurouracil, rapamycin, a transforming growth factor (TGF) antibody, an immunesuppresive agent, and heparin. The transforming growth factor (TGF) antibody may be selected from the group consisting of TGF-B 2 monoclonal antibody, Interlukin 1 or 6 antibody, and a cytokine antibody, and the immunesuppresive agent may be selected from the group consisting of cyclosporin and FK57.

In some embodiments, the antifibrotic agent is selected from the group consisting of an antifibrotic drug such as mitomycin-C, 5-flurouracil, or rapamycin, a transforming growth factor (TGF) antibody such as TGF-B 2 monoclonal antibody, Interlukin 1, or 6 antibody, an immunesuppresive agent such as cyclosporin or FK57, heparin, and combinations thereof.

The term "anticancer agent" as used herein refers to a compound or substance that can kill cancerous cells or inhibit cancer cell function. Anticancer agents include alkylating agents such as mechlorethamine, nitrosoureas (carmustine, lomustine), melphalan, cyclophosphamide, busulfan and procarbazine, antimetabolites such as methotrexate, 6-thioguanine, 5-fluorouracil, 6-mercaptopurine, cytosine arabinoside, gemcitabine, fludarabine and capecitabine, antimitotics such as vincristine, vinblastine, paclitaxel and docetaxel, hormones such as estrogens, prednisone, goserelin, anti-estrogen (tamoxifen), flutamide, leuprolide, immunosuppressives such as azathioprine, tacrolimus (FK506), cyclosporin a, natural products such as dactinomycin, bleomycin, camptothecin and analogs (e.g., irinotecan and topotecan), daunorubicin, mitomycin C, doxorubicin, etoposide (V P-16), and other agents such as hydroxyurea, asparaginase, amsacrine, cisplatin, carboplatin, mitoxantrone and imatinib.

In some embodiments, the anticancer agent is selected from the group consisting of an alkylating agent such as mechlorethamine, nitrosoureas (carmustine, lomustine), melphalan, cyclophosphamide, busulfan, or procarbazine, an antimetabolite such as methotrexate, 6-thioguanine, 5-fluorouracil, 6-mercaptopurine, cytosine arabinoside, gemcitabine, fludarabine, or capecitabine, an antimitotic such as vincristine, vinblastine, paclitaxel, or docetaxel, a hormone such as estrogen, prednisone, goserelin, anti-estrogen (tamoxifen), flutamide, or leuprolide, an immunosuppressive such as azathioprine, tacrolimus (FK506), or cyclosporin a, dactinomycin, bleomycin, camptothecin and analogs (e.g., irinotecan and topotecan), daunorubicin, mitomycin C, doxorubicin, etoposide (V P-16), hydroxyurea, asparaginase, amsacrine, cisplatin, carboplatin, mitoxantrone, imatinib, and combinations thereof.

Discomfort reducing agents may function to reduce pain and/or discomfort in a subject. Discomfort reducing agents include antispasmodic agents such as alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiver inium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stiloniumiodide, sultroponium, tiemonium iodide, tiquiZium bromide, tiropramide, trepibutone, tricromyl, trifolium, trimebutine, n,n-1 trimethyl-3,3-diphenyl-propylamine, tropenZile, trospium chloride, and xenytropium bromide, among others, as well as combinations and pharmaceutically acceptable salts; alpha-adrenergic blockers such as alfuzosin, amosulalol, arotinilol, dapiprazole, doxazosin, ergoloid mesylates, fenspiride, idazoxan, indoramin, labetalol, manotepil, naftopidil, nicergoline, prazosin, tamsulosin, terazosin, tolazoline, trimazosin, and yohimbine.

Of these, tamsulosin, alfuzosin, doxazosin, prazosin, tamsulosin and terazosin are alpha-1-adrenergic blockers, of which tamsulosin and alfuzosin are selective alpha-1-adrenergic blockers.

Other examples of a discomfort reducing agent include corticosteroids such as betamethasone, cortisone, dexamethasone, defazacort, hydrocortisone, methylprednisolone, prednisolone, prednisone and triamcinolone; narcotic analgesic agents including codeine, morphine, fentanyl, meperidine, propoxyphene, levorphanol, oxycodone, oxymorphone, hydromorphone, pentazocine, and methadone; non-narcotic analgesic agents including acetaminophen, and non-steroidal anti-inflammatory drugs such as aspirin, diflunisal, salsalate, ibuprofen, ketoprofen, naproxen, indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib; local anesthetic agents including benzocaine, cocaine, lidocaine, triclosan, mepivacaine, and novacaine, among others, as well as combinations and pharmaceutically acceptable salts, esters and derivatives of the aforementioned.

In some embodiments, the discomfort reducing agent is selected from the group consisting of an antispasmodic agent, an alpha-adrenergic blocker, a corticosteroid, a narcotic analgesic agent, a non-narcotic analgesic agent, a non-steroidal anti-inflammatory drug, a local anesthetic agent, combinations thereof, pharmaceutically acceptable salts thereof, esters thereof, and derivatives thereof.

The term "antibacterial agent", otherwise termed herein as "antibiotic agent", refers to compounds or substances which are able to inhibit, reduce or prevent growth of bacteria, as well as to decrease infectivity or virulence of the bacteria. Examples of antibacterial agent include, but are not limited to, mitomycin-C, bleomycin, dactinomycin, plicatomycin, and anthracyclines such as doxorubicin, daunorubicin, epirubicin, idarubicin, or anthracenedione.

In specific embodiments, the active agent is mitomycin C, paclitaxel, triclosan, or combinations thereof.

The swellable coating may be disposed on at least a portion of an exterior surface of the stent. In some embodiments, the swellable coating is disposed on a substantial portion of or substantially all of an exterior surface of the stent. The term "exterior surface" as used herein refers to the outside surface of the stent, as opposed to within the vascular luminal interior space.

Optionally, the stent assembly comprises a carrier that is dispersed in the swellable coating and/or disposed on at least a portion of an exterior surface of the stent. As used herein, the term "carrier", otherwise termed herein as a "delivery agent", refers to any carrier compound or agent useful and/or effective for delivering the particular or desired active agent. Where a carrier is present, the carrier may be dispersed in the swellable coating and/or disposed on at least a portion of an exterior surface of the stent.

The carrier may be formed from a variety of suitable materials, including all polymeric materials. In some embodiments, the carrier may comprise or consist of a biodegradable polymer. In specific embodiments, the carrier is formed of a biodegradable polymer. The terms "biodegradable", "bioabsorbable", and "bioresorbable" are used interchangeably herein, and refer generally to a substance which can be broken down by microorganisms, or which spontaneously breaks down over a relatively short time (within 2-15 months) when exposed to environmental conditions commonly found in nature.

Examples of polymers that may be considered biodegradable include aliphatic polyesters, poly(amino acids), copoly (ether-esters), polyalkylenes oxalates, polyamides, poly (iminocarbonates), polyorthoesters, polyoxaesters, polyamidoesters, polyoxaesters containing amido groups, poly(anhydrides), polyphosphazenes, polycarbonates, naturally-occurring biodegradable polymers such as chitosan, collagen, starch, and blends thereof. Examples of polyortho esters include a polylactide, a polyglycolide, a polycaprolactone, a polylactic acid, a biodegradable polyamide, a biodegradable aliphatic polyester, and/or copolymers thereof, or with other biodegradable polymers such as those mentioned above.

In some embodiments, the biodegradable polymer is selected from the group consisting of polycaprolactone (PCL), poly-(D,L-lactide-co-caprolactone) (PLC), poly-L-lactide (PLLA), poly-D-lactide (PDLA), polyglycolide (PGA), polylactic acid (PLA), polycaprolactone-polylactic acid copolymer (PCL-PLA copolymer), polylactide-polyglycolide copolymer (PLGA), poly(trimethylene carbonate) (TMC); copolymers of polycaprolactone (PCL) and poly(trimethylene carbonate) (TMC); triblock copolymers of polylactic acid (PLA), polycaprolactone (PCL) and/or poly(trimethylene carbonate) (TMC); polylactic acid-polyethylene oxide copolymers, polygluconate polyhydroxybutyrate, polyanhydride, polyphosphoester, poly(amino acids), polydioxanone, cellulose, collagen, chitosan, copolymers thereof, and combinations thereof.

In specific embodiments, the carrier comprises a material selected from the group consisting of poly-L-lactide-co-caprolactone, polylactide-polyglycolide copolymer, copolymers thereof, and combinations thereof.

The carrier may be present as one or more particles and/or one or more layers disposed (a) between the stent and the swellable coating, (b) within the swellable coating, and/or (c) on the swellable coating. The carrier may, for example, be a single, or multiple thin polymeric coating disposed in between the stent and the swellable coating. Advantageously, this allows a more even controlled release of active agent comprised in the carrier.

In some embodiments, the carrier comprises particles. The carrier particles may be disposed between the stent and the swellable coating, within the swellable coating, and/or on the swellable coating. In some embodiments, the carrier comprises particles disposed within the swellable coating.

Size of the particles may be in the range of about 20 nm to about 1000 nm, or about 1000 nm to 1000 more typically about 20 nm to about 100 µm, or about 100 nm to about 100 µm. For example, size of the particles may be in the range of about 200 nm to about 100 µm, such as about 500 nm to about 100 µm, about 800 nm to about 100 µm, about 1 µm to about 100 µm, about 20 µm to about 100 µm, about 50 µm to about 100 µm, about 75 µm to about 100 µm, about 100 nm to about 80 µm, about 100 nm to about 60 µm, about 100 nm to about 40 µm, about 100 nm to about 20 µm, about 100 nm to about 1 µm, about 1 µm to about 50 µm, or about 10 µm to about 60 µm.

In some embodiments, the carrier is present as one or more layers disposed on an at least a portion of an exterior surface of the stent. For example, the one or more layers comprising the carrier may be disposed between the stent and the swellable coating, within the swellable coating, and/or on the swellable coating.

Thickness of the one or more layers may be in the range of about 1 µm to about 3000 more typically in the range of about 10 µm to about 1000 For example, thickness of the one or more layers may be in the range of about 10 µm to about 1000 µm. For example, thickness of the one or more layers may be in the range of about 50 µm to about 1000 µm, such as about 100 µm to about 1000 µm, about 300 µm to about 1000 µm, about 500 µm to about 1000 µm, about 750 µm to about 1000 µm, about 10 µm to about 800 µm, about 10 µm to about 600 µm, about 10 µm to about 500 µm, about 10 µm to about 300 µm, about 50 µm to about 800 µm, or about 100 µm to about 500 µm.

In specific embodiments, the carrier is present as one or more layers disposed between the stent and the swellable coating. The one or more layers may comprise or consist of a thermoplastic elastomer, such as styrenic block copolymers, polyolefin blends, elastomeric alloys, thermoplastic polyurethanes, thermoplastic copolyesters and thermoplastic polyamides. More specific examples include polyester-based polyurethanes, polyether-based polyurethanes, polyolefin-based polyurethanes, polyester-polyether copolymers such as poly[dimethyl terephthalate]-poly[tetramethylene ether glycol] block copolymers and poly [butylene terephthalate]-poly[tetramethylene oxide] block copolymers, and polystyrene-polyolefin block copolymers such as poly(styrene-b-polyethylene/butylene-b-polystyrene) (SEBS) and poly(styrene-b-isobutylene-b-styrene)triblock copolymers (SIBS), and polyether-polyamide block copolymers such as poly[tetramethylene oxide]-block-polyimide-12 block copolymers.

The thermoplastic elastomer comprised in the one or more layers may have at least the same as or a higher elongation at break than the material comprised in the stent such as the stent body and/or retention structures.

Most bioabsorbable polymers available today, such as polylactic acids (PLA), polycaprolactone (PCL) and polylactic-co-glycolic acid (PLGA) display a very similar mechanical behavior, with a high Young's modulus and rather low elongation at break values. Sometimes, these polymers may seem, in a pure form, unsuited for use where highly flexible materials are required because of clinical needs. In some embodiments, one or more of the above-mentioned polymers may be blended with another polymer or copolymerized with another polymer, where the copolymerization may facilitate a broad range of properties, including good mechanical strength, biocompatibility, biodegradability, and processability, to render the polymers excellent materials for medical application.

The active agent is comprised in at least one of the swellable coating or the carrier, if present. As mentioned above, in embodiments wherein a carrier is not present, the active agent is comprised in the swellable coating only. An active agent that is loaded in the swellable coating may be delivered to the intended site on a subject to allow fast release of the active agent to the subject.

In embodiments where a carrier is present, at least a portion of the active agent may be comprised in the carrier for controlled release of the active agent from the carrier. This means that the active agent may be comprised or present in both the swellable coating and the carrier. By loading the active agent in the swellable coating and in the carrier, loading of the active agent in the stent assembly may be increased. The active agent that is loaded in the swellable coating may be different from the active agent that is loaded in the carrier, which may in turn allow customization of active agent(s) administered to the subject. In further embodiments, the active agent may be comprised in the carrier only. The versatility of active agent loading allows tailoring of the stent assembly to suit individual needs of patient and intended application requirements of the stent.

Amount of the active agent in the carrier may be in the range of about 2 wt % to about 25 wt % of the carrier. For example, amount of the active agent in the carrier may be in the range of about 3 wt % to about 25 wt %, about 5 wt % to about 25 wt %, about 7 wt % to about 25 wt %, about 12 wt % to about 25 wt %, about 18 wt % to about 25 wt %, about 2 wt % to about 18 wt %, 2 wt % to about 10 wt %, about 2 wt % to about 6 wt %, about 2 wt % to about 5 wt %, about 5 wt % to about 20 wt %, about 9 wt % to about 18 wt %, about 3 wt % to about 8 wt %, about 4 wt % to about 6 wt %, or about 4 wt % to about 9 wt %.

Various embodiments refer in a further aspect to use of a stent assembly according to the first aspect as a ureteric stent.

As mentioned above, the stent assembly disclosed herein is able to inhibit ureteral fibroblast proliferation so as to prevent stricture recurrence. A swellable coating, which is able to swell up to 1500 times its volume when in contact with a liquid medium, is disposed on at least a portion of an exterior surface of a stent. One or more active agents may be incorporated in the swellable coating. Under urinary conditions, for example, the ureteric stent may swell towards and/or be in contact with ureter wall to enhance localized delivery of the active agent(s). In addition or alternatively, a carrier may be comprised in the stent assembly, such that by incorporating an active agent in the carrier, controlled release of the active agent may take place. As the swellable coating may be applied on an existing conventional stent, this provides greater ease of acceptance by patients and practitioners since the protocols at which the stents are used may remain unchanged. Advantageously, the stent assembly provides greater versatility in use, since, depending on where the active agent is located, active agent may be dispensed from the stent assembly in a quick release form (when it is incorporated in the sweallable coating), or in a controlled release form (when it is incorporated in the carrier).

In a third aspect, a method of preparing a stent assembly is provided. The method comprises providing a stent. Suitable stents that may be used have already been discussed above.

In various embodiments, providing a stent comprises at least one of physically treating or chemically treating an exterior surface of the stent.

Physically treating an exterior surface of the stent may comprise texturing the exterior surface of the stent, for example, to impart a topography or pattern onto the surface. In so doing, physical bonding sites may be formed on the stent surface, which may improve physical bonding or adhesion between the stent surface and the swellable coating. In some embodiments, texturing the exterior surface of the stent is carried out by etching such as wet or dry etching, and/or roughening the exterior surface with solid particles.

Chemically treating an exterior surface of the stent may be carried out by plasma treatment. By plasma coating the surface, chemical bonding sites may be formed. In various embodiments, the plasma treatment comprises a first step of oxygen plasma and a second step of nitrogen plasma. By carrying out the plasma treatment, primary and/or secondary amino groups which are hydrophilic may be fixed on a surface of the stent to allow interaction or bonding with functional groups of a swellable material comprised in the swellable coating.

In various embodiments, the first step of oxygen plasma may involve either a chemical oxidation treatment, or exposing the stent surface to oxygen-containing gases, optionally in the presence of argon (Ar) and/or other inert gases, to generate free radicals.

The second step of nitrogen plasma may involve exposing the stent surface to plasma gases containing nitrogen atoms to form amino groups. Examples of suitable plasma gases containing nitrogen atoms include ammonia, primary and secondary amines, nitrous oxide, nitrogen, other gases containing nitrogen moieties, and mixtures of such gaseous compounds.

The method of preparing a stent assembly comprises disposing a swellable material on the stent. The swellable material may be disposed on a stent surface which has been physically and/or chemically treated, and which thereby contains suitable physical bonding sites and/or chemical bonding sites. Examples of suitable swellable material that may be used have already been discussed above.

Disposing a swellable material on the stent optionally comprises dispersing a carrier in the swellable material and/or disposing a carrier on at least a portion of an exterior surface of the stent, and incorporating an active agent in at least one of the swellable material or the carrier, if present, to form a swellable coating on at least a portion of an exterior surface of the stent. Examples of suitable carrier that may be used have already been discussed above.

In some embodiments, disposing the swellable material on the stent comprises applying a liquid reagent comprising the swellable material and an active agent on at least a portion of an exterior surface of the stent. As mentioned above, the active agent may be comprised or incorporated in the swellable coating only, such as in the case where a carrier is not present or a carrier is not loaded with the active agent. An active agent that is loaded in the swellable coating may be delivered to the intended site on a subject to allow fast release of the active agent to the subject.

An active agent is incorporated in at least one of the swellable material or the carrier, if present, to form a swellable coating on at least a portion of an exterior surface of the stent. Examples of suitable active agent have already been discussed above.

In various embodiments, disposing a swellable material on the stent comprises dispersing a carrier in the swellable material and/or disposing a carrier on at least a portion of an exterior surface of the stent.

In some embodiments, the method of preparing a stent assembly comprises incorporating the active agent in both the swellable material and the carrier. In specific embodiments, the method of preparing a stent assembly comprises incorporating the active agent in the carrier only. As mentioned above, the active agent may be incorporated in the swellable material, for example, by dispersing the active agent in a suspension or solution comprising the swellable material prior to forming the swellable coating. Likewise, incorporating the active agent in the carrier may comprise dispersing the active agent in a suspension or solution comprising the carrier, so as to disperse the active agent in the carrier or to coat the active agent on the carrier, followed by forming the carrier.

Disposing the swellable material on the stent may be carried out by a method selected from the group consisting of spraying, brushing, dip coating, molding, electrodeposition, and combinations thereof.

In some embodiments, the swellable material comprises or consists of a hydrogel. Disposing a swellable material on the stent may further comprise cross-linking a hydrogel-forming agent to form the hydrogel. Examples of hydrogel-forming agents have been discussed above. Examples of suitable crosslinking techniques include physical crosslinking, chemical crosslinking, radiation crosslinking, or combinations thereof.

Physically cross-linking may take place via, for example, complexation, hydrogen bonding, desolvation, van der Waals interactions, or ionic bonding. In various embodiments, a hydrogel may be formed by self-assembly of one or more types of hydrogel-forming agents in an aqueous medium. The term "self-assembly" refers to a process of spontaneous organization of components of a higher order structure by reliance on the attraction of the components for each other, and without chemical bond formation between the components. For example, polymer chains may interact with each other via any one of hydrophobic forces, hydrogen bonding, Van der Waals interaction, electrostatic forces, or polymer chain entanglement, induced on the polymer chains, such that the polymer chains aggregate or coagulate in an aqueous medium to form a three-dimensional network, thereby entrapping molecules of water to form a hydrogel. Examples of physically cross-linkable polymer that may be used include, but are not limited to, gelatin, alginate, pectin, furcellaran, carageenan, chitosan, derivatives thereof, copolymers thereof, and mixtures thereof.

Chemical cross-linking may take place in the presence of a chemical cross-linking agent. In some embodiments, cross-linking the hydrogel-forming agent is carried out by contacting the hydrogel-forming agent with a cross-linking agent. The term "chemical cross-linking agent" refers to an agent which induces chemical cross-linking. The chemical cross-linking agent may be any agent that is capable of inducing a chemical bond between adjacent polymeric chains. For example, the chemical cross-linking agent may be a chemical compound. Examples of chemical compounds that may act as cross-linking agent include, but are not limited to, 1-ethyl-3-[3-dimethylaminopropyl]carbodiimide hydrochloride (EDC), vinylamine, 2-aminoethyl methacrylate, 3-aminopropyl methacrylamide, ethylene diamine, ethylene glycol dimethacrylate, methymethacrylate, N,N'-methylene-bisacrylamide, N,N'-methylene-bis-methacrylamide, diallyltartardiamide, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate, diallyl phthalate, transglutaminase, derivatives thereof or mixtures thereof.

In some embodiments, the hydrogel-forming agents are themselves capable of chemical or physical cross-linking without using a cross-linking agent.

Besides the above-mentioned, the hydrogel-forming agents may be cross-linked using a cross-linking agent in the form of an electromagnetic wave. The cross-linking may be carried out using an electromagnetic wave, such as gamma or ultraviolet radiation, which may cause the polymeric chains to cross-link and form a three-dimensional matrix, thereby entrapping water molecules to form a hydrogel. The swellable material may further comprise a photoinitiator to allow cross-linking by irradiation. An example of a photoinitiator is IRGA CURE brand initiator available from Ciba Specialty Chemicals.

Therefore, choice of cross-linking agent is dependent on the type of polymeric chain and functional group present, and a person skilled in the art would be able to choose the appropriate type of cross-linking agent accordingly.

In various embodiments, cross-linking the hydrogel-forming agent is carried out by irradiating the hydrogel-forming agent with electromagnetic radiation. Examples of electromagnetic radiation that may be used include radio waves, microwaves, terahertz radiation, infrared radiation, light such as visible light, ultraviolet light, and infrared light, X-rays and gamma rays. In some embodiments, the electromagnetic radiation is ultraviolet or blue light, collectively referred to herein as "UV/Vls radiation", which may have a wavelength in the range from about 240 nm to about 380 nm. In specific embodiments, the electromagnetic radiation has a wavelength of about 365 nm.

Irradiating the hydrogel-forming agent with electromagnetic radiation may be carried out for any suitable time period. For example, irradiating the hydrogel-forming agent with electromagnetic radiation may be carried out for a time period in the range of about 1 minute to about 15 minutes, such as about 5 minutes to about 15 minutes, about 8 minutes to about 15 minutes, about 10 minutes to about 15 minutes, about 1 minute to about 12 minutes, about 1 minute to about 8 minutes, or about 8 minutes to about 12 minutes.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Various embodiments disclosed herein relate to an improved ureteric stent, with object to inhibit ureteral fibroblast proliferation so as to prevent stricture recurrence. The stent described herein comprises a swellable coating, which is able to swell up to 1500 times its volume, more typically 5 to 160 times its volume, when in contact with a medium. Advantageously, the ureteric stent may swell towards and/or be in contact with ureter wall under urine conditions, which may work to enhance localized drug delivery. The swellable coating may be applied on an existing conventional stent. The medium may comprise at least one urological beneficial agent, such as anti-fibrotic drugs. In some embodiments, the swellable coating further comprises at least one polymeric delivery platform, otherwise termed herein as a carrier. The polymeric delivery platform may act in conjunction with the urological beneficial agent, otherwise termed herein as active agent, to control release of the agent.

Hydrogel swelling may be used to enhance the localized delivery of drugs into tissues. The drugs may be an anti-fibrotic drug, an anti-bacteria drug, an anti-cancer drug, or a multifunctional drug having two or more of the above-mentioned properties. Treatment may be terminated by simply removing the stent. Coating may be applied onto any commercially available ureteric stent surface. Advantageously, the improved ureteric stent disclosed herein is not disruptive to established physician practice/workflow, and new skills or reimbursement codes are not required.

Also disclosed herein is a method for manufacturing a coated ureteric stent, which may exhibit the swelling characteristics mentioned above. The method may include the steps of physically treating the stent surface to form physical bonding on the surface of stent, chemically treating the surface to form chemical bonding on the surface of the stent, coating the modified surface with a hydrogel, and crosslinking the hydrogel to form a hydrogel coating on the drug eluting layer to form the swellable coating.

In various embodiments, the method comprises coating the ureteric stent with a swellable layer comprising a urological beneficial agent. In some embodiments, the method comprises incorporate the drug delivery platform loaded with a urological beneficial agent.

Advantageously, the ureteric stent with a unique swellable coating is able to swell in urine condition, which functions to effectively enhance the localized drug delivery thereby increasing efficacy of the treatment. Further, the unique swellable coating may easily be applied on any commercial-available ureteric stent surface without the need to produce a special stent and delivery system, which would increase costs. The treatment may easily be terminated by removing the stent. In addition, the swellable coating ureteric stent disclosed herein may readily be incorporated into current practice, and is expected to be readily accepted by both urologists and patients since the stents used and procedures/protocols employed are unchanged.

Example 1

In the first example, 7.5% of mitomycin C (MMC) was incorporated into poly-L-lactide-co caprolactone (PLC70/30). This formulation was then coated onto the stent as drug delivery coating. Then the drug coated stent was plasma treated with oxygen for 5 minutes at 100 W and 30 sec. Finally, 7.5% PEGDA with 0.2% Irgacure water solution was coated onto the plasma modified drug coated stent, was exposed to 365-nm UV light (6 W) for 5 minutes from a 1-cm distance while the stent was manually rotated slowly.

Figure 7:
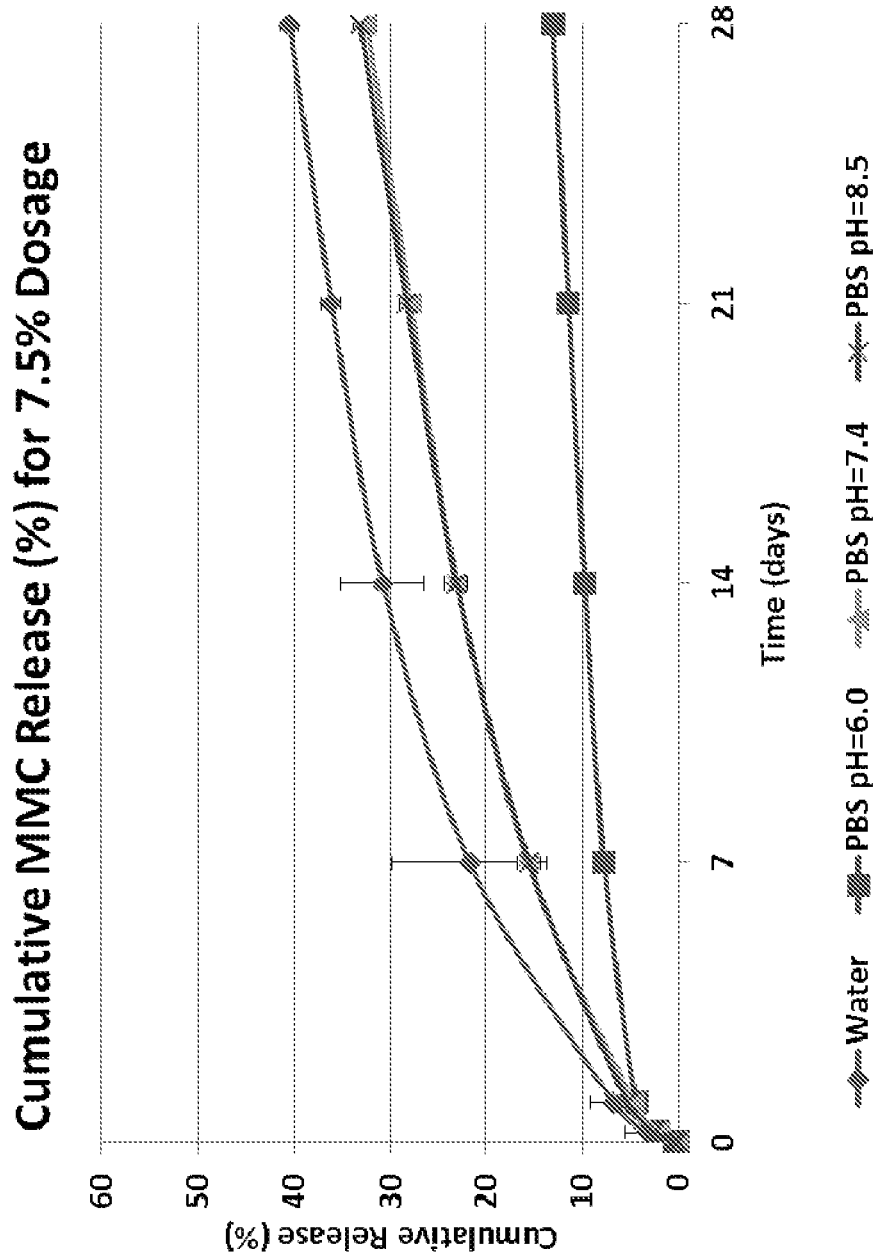
FIG. 7 is a graph showing cumulative mitomycin-C (MMC) (7.5% dosage) drug release profile from a bilayer coated stent of embodiment at 37° C. in water, and buffer solution (pH=6.0, pH=7.4, and pH=8.5).

Both drug delivery coating and swellable coating gave a uniform coating that can control the release of the MMC over 28 days in variety urinary condition pH from 6 to 8.5, as shown in FIG. 7.

Example 2

Figure 8:
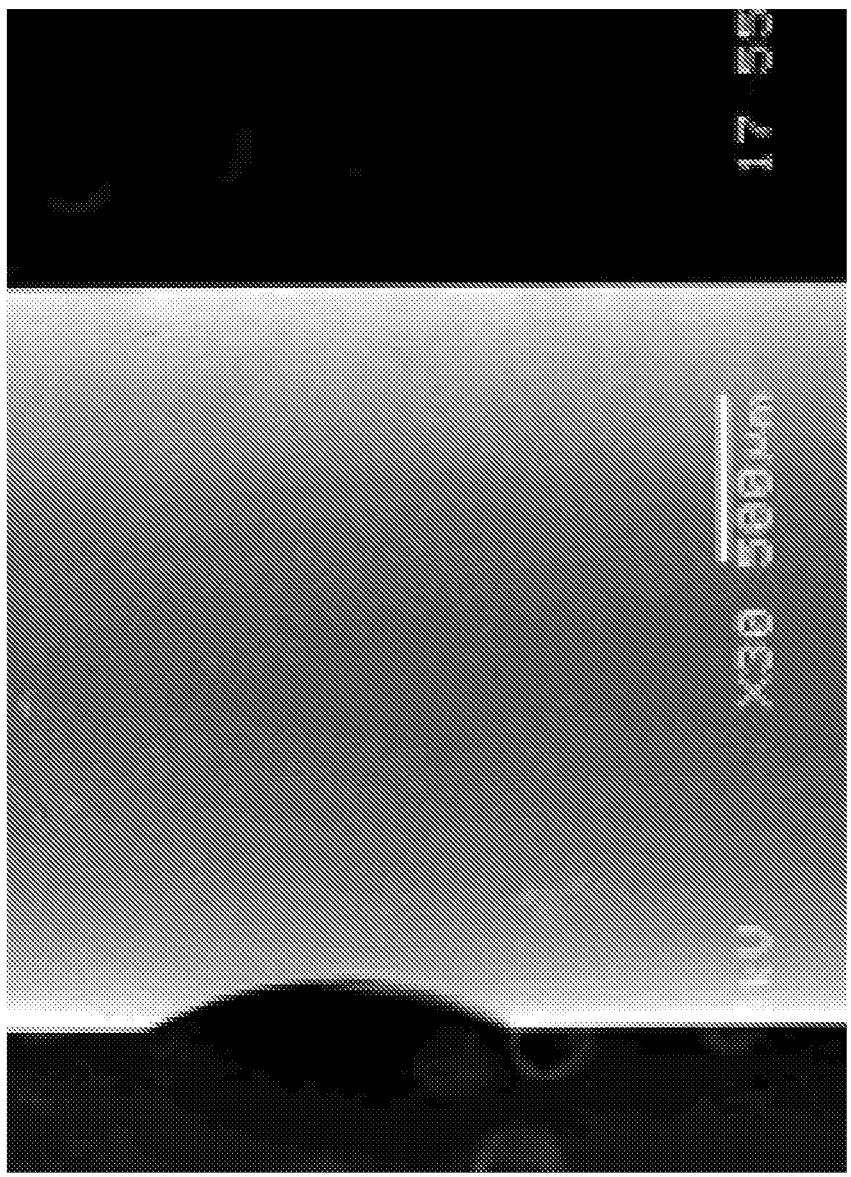
FIG. 8 shows a scanning electron microscopy (SEM) image of a swellable coating ureteric stent according to an embodiment. Scale bar in the figure denotes 500 μm.
Figure 9:
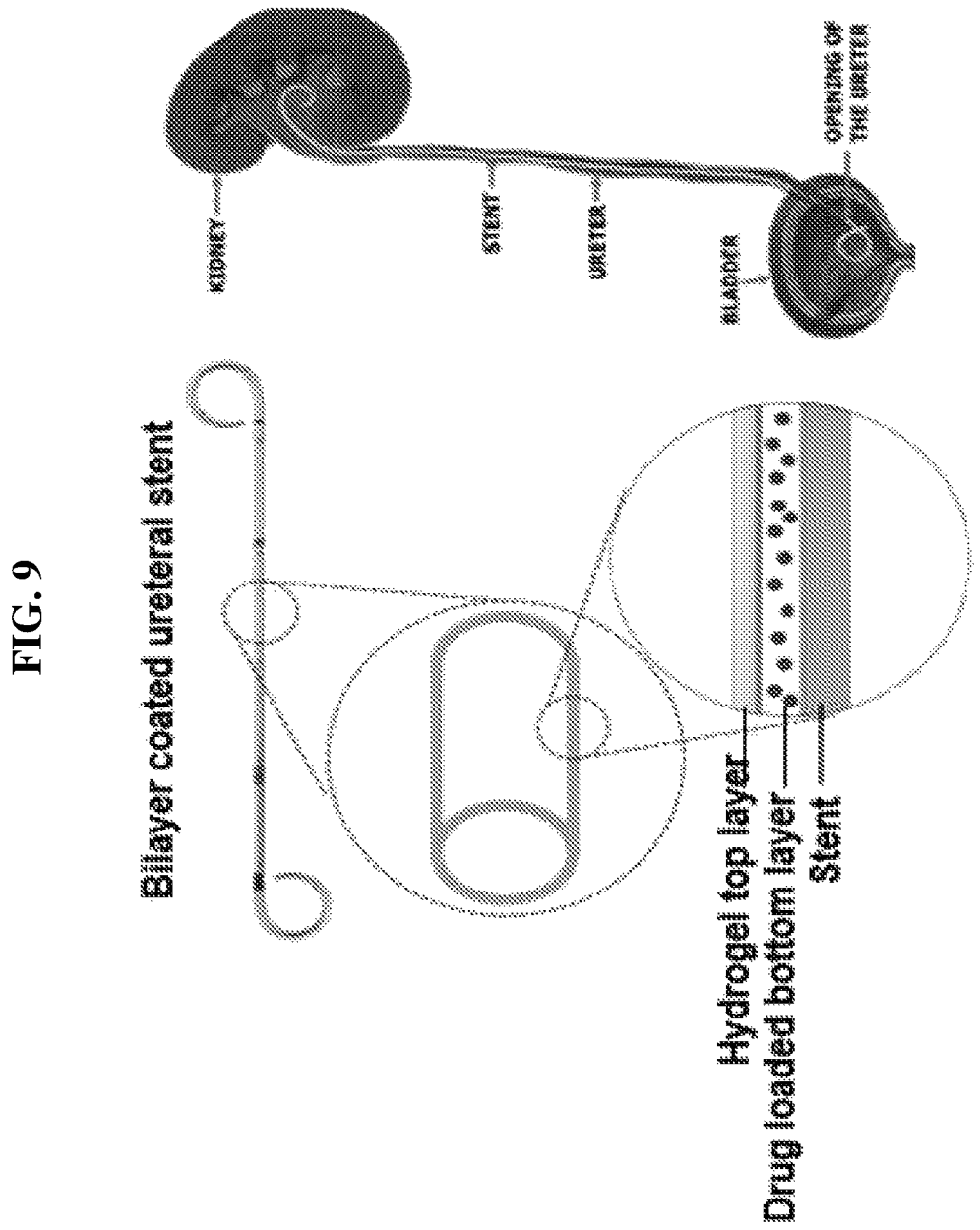
FIG. 9 shows a bilayer coated ureteral stent according to an embodiment. As shown in the figure, the stent comprises a drug loaded bottom layer that is in contact with the stent, and a hydrogel top layer that is in contact with the drug loaded bottom layer. The drug may be an anti-proliferative drug, an anti-cancer drug, an anti-bacteria drug, or a multifunctional drug having two or more of the above-mentioned properties. The polymer may provide sustained delivery of the drugs effectively and safely over indwelling duration. The hydrogel may serve to maximize localization of drug transfer into urothelial tissues to overcome its high impermeability of drugs penetration.
Figure 10:
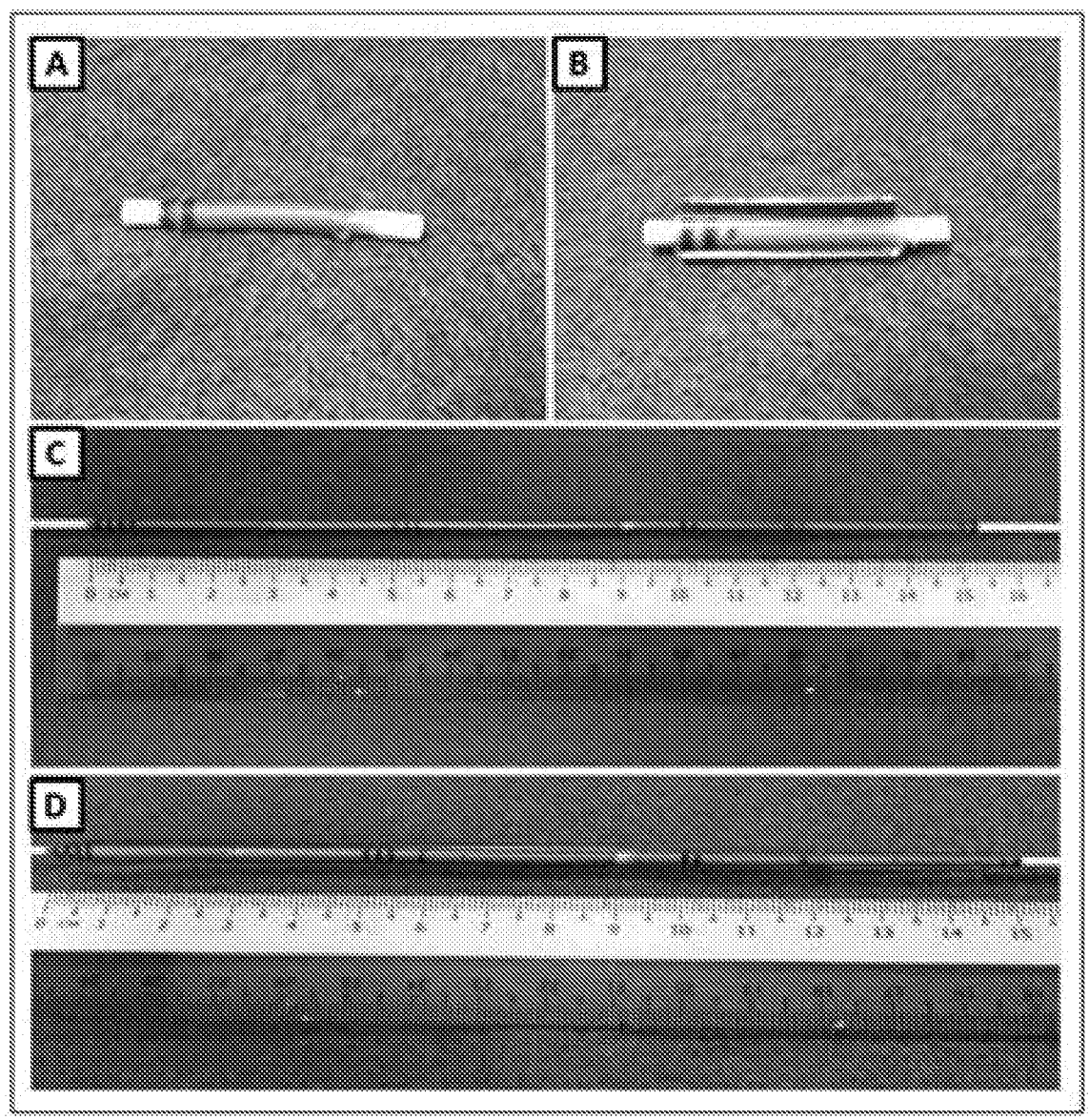
FIG. 10(A) to (D) are photographs depicting the working prototypes prepared.
Figure 12:
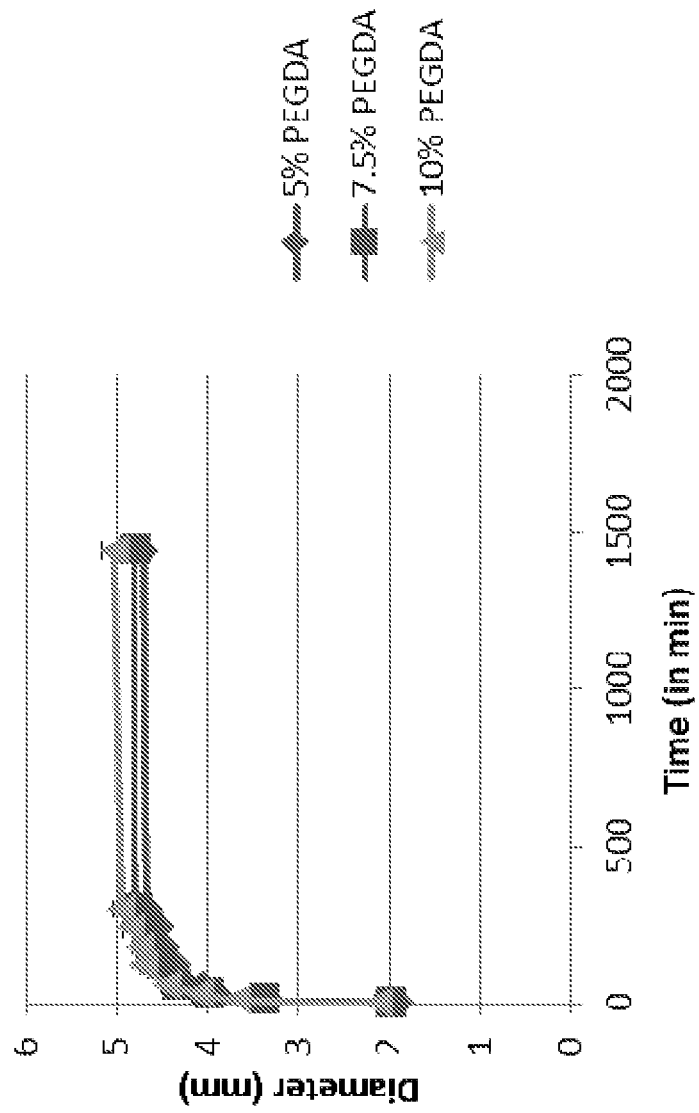
FIGS. 12(A) and (B) are graphs showing (A) diameter of coated section (mm) vs time; and (B) change in thickness of PEGDA (mm) vs time, for 5% PEGDA, 7.5% PEGDA, and 10% PEGDA. The hydrogel coating of the stent is able to swell upon contact and absorption of water. The graph illustrate that the coating is able to swell up to comparable ureteric diameter of 4.5 mm to 5 mm within 30 min to 1 h under the static condition where the stent is immersed in water. TABLE 1 below shows the results
Figure 12:
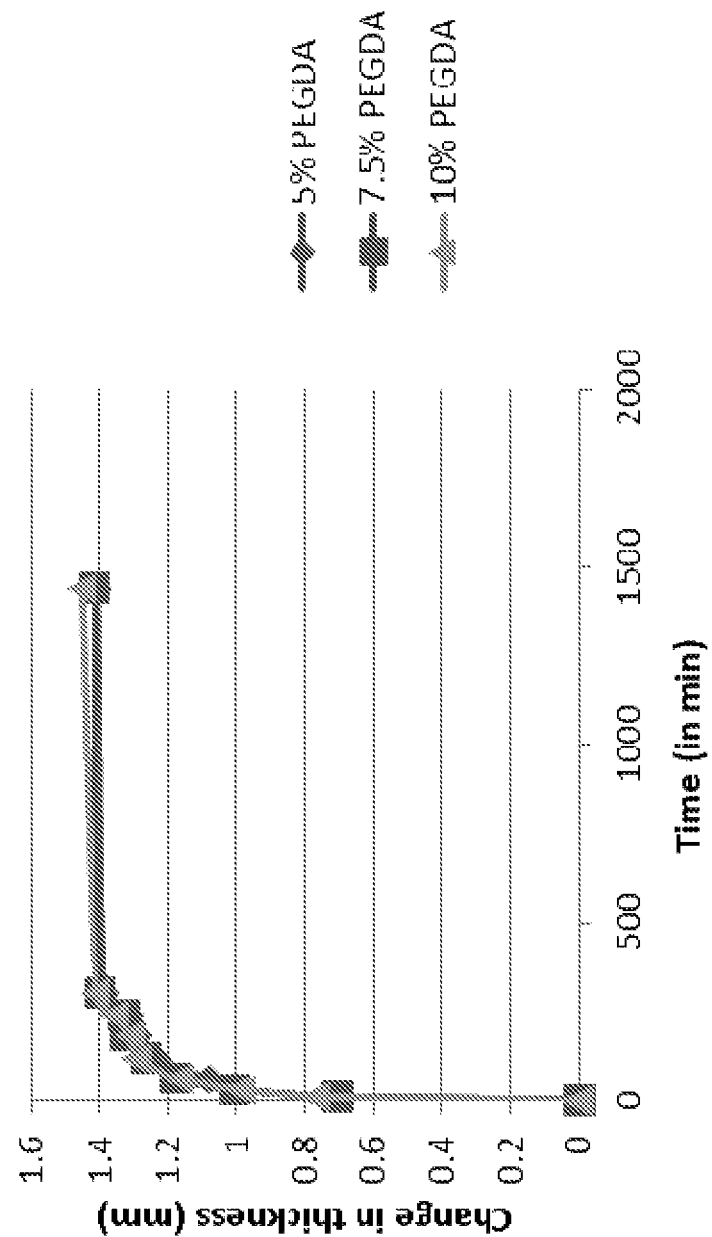

In the second example, the stent of polyurethane was plasma treated with oxygen for 5 minutes at 100 w at 2 minutes. 10% of paclitaxel was pre-loaded into PLGA particles, then blended with 1% methacrylated hyaluronic acid (HAMA) solution with 2% Igacure water solution, was coated onto the plasma treated surface of stent, was exposed to 365-nm UV light for 15 minutes. The coating surface is smooth, as shown in FIG. 8.

Example 3

In the third example, the 5% 5-Flurouracil was loaded into poly-L-lactide-co-caprolaction solution, coated onto stent to form the drug delivery coating. 10% triclosan was preloaded into PLGA particles, blended with 5% PEGDA solution with 0.1% Igacure waster solution, was coated onto pre-treated surface of PLC loaded with 5-Flurouracil, was exposed to 365-nm UV light for 10 minutes.

Example 4

Cell Work

In each well of a 96 well cell culture plate, 3000 human bladder stroma fibroblasts cells are seeded. After one day of seeding, different concentrations of mitomycin C dissolved in cell media (200 µL) were added to the well. After 3 days of drug treatment, the drug media was removed and the well added with 70 µL of a cell viability reagent, prestoblue, in the ratio of 9:1 (cell media: prestoblue). It was found that the minimum concentration of MMC required to cause death of human bladder stroma fibroblasts was 0.01 µg/mL, i.e. 0.01 µg/mL of MMC was required to inhibit the fibroblast proliferation. $GI_{50}$ was measured at $10^{0.94}$ µg/mL, or about 0.115 µg/mL.

Example 5

Effect of MMC-Eluting Ureteral Stents on Fibroblast Inhibition

For each of the well of a 24 well cell culture plate, 12000 human bladder stroma fibroblast cells were seeded. After 1 day of seeding, the respective stent samples were placed in a cell culture insert in the well, such that there was no direct contact between the stents and the cells. Prior to this, the stents were sterilized with ethylene oxide gas. It was found that the stent (polyurethane), polymer and hydrogel do not affect or inhibit the fibroblasts cells, whereas the drug-coated stents were able to reduce the proliferation of the cells significantly. There was a slightly higher inhibition of cell proliferation for Sample 5 compared to Sample 4 due to the larger amount of drugs released in the initial few hours in the hydrogel coated stent.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A stent assembly consisting of:
   a stent, wherein the stent is a tube or a helical coil;
   a first carrier comprising a first active agent, wherein the first carrier is disposed as one or more layers on at least a portion of an exterior surface of the stent; and
   a swellable coating comprising a second active agent, wherein the swellable coating further comprises a second carrier comprising a third active agent, wherein the second carrier is in a form of particles, wherein the swellable coating is disposed on at least a portion of the one or more layers of the first carrier, wherein the swellable coating swells by 5 times to 160 times its volume under urinary conditions to make contact with a ureter wall of a subject.

2. The stent assembly according to claim 1, wherein the swellable coating comprises a swellable material selected from the group consisting of a hydrogel, a water swellable polymer, a superabsorbent polymer, copolymers of the water swellable polymer and the superabsorbent polymer, and combinations thereof.

3. The stent assembly according to claim 1, wherein the first, second and third active agents are independently selected from the group consisting of an antifibrotic agent, an anticancer agent, a discomfort reducing agent, an antibacterial agent, a gene, a gene vector, a growth factor, and combinations thereof.

4. The stent assembly according to claim 1, wherein amount of the first active agent in the first carrier is in the range of about 2 wt % to about 25 wt % of the carrier.

5. The stent assembly according to claim 1, wherein the one or more layers has a thickness in the range of about 10 µm to about 1000 µm.

6. The stent assembly according to claim 1, wherein the one or more layers comprises a thermoplastic elastomer.

7. A method of preparing a stent assembly of claim 1, the method comprising:
   providing a stent, wherein the stent is a tube or a helical coil;
   disposing a swellable coating on the stent, wherein the swellable coating is adapted to swell by 5 times to 160 times its volume under urinary conditions to make contact with a ureter wall of a subject; and
   disposing a first carrier on at least a portion of an exterior surface of the stent,
   wherein the first carrier comprises a first active agent, and
   wherein the swellable coating comprises a swellable material and a second active agent, the swellable coating further comprises a second carrier comprising a third active agent, the second carrier being in a form of particles.

8. The method according to claim 7, wherein providing the stent comprises physically treating the exterior surface of the stent by etching, and/or roughening the exterior surface with solid particles.

9. The method according to claim 7, wherein providing the stent comprises chemically treating the exterior surface of the stent with plasma treatment.

10. The method according to claim 7, wherein disposing the swellable coating on the stent comprises applying a liquid reagent comprising the swellable material and the second active agent on at least the portion of the exterior surface of the stent.

11. The method according to claim 7, wherein disposing the first carrier comprises dispersing the first carrier on the exterior surface of the stent.

12. The method according to claim 7, wherein the swellable material comprises a hydrogel.

13. The method according to claim 12, wherein disposing the swellable coating on the stent further comprises cross-linking a hydrogel-forming agent to form the hydrogel.

14. The method according to claim 13, wherein the swellable material further comprises a photoinitiator.

* * * * *